(12) United States Patent
Dorsch et al.

(10) Patent No.: US 9,376,433 B2
(45) Date of Patent: Jun. 28, 2016

(54) (AZA-)ISOQUINOLINONE DERIVATIVES

(71) Applicant: MERCK PATENT GMBH, Darmstadt (DE)

(72) Inventors: Dieter Dorsch, Ober-Ramstadt (DE); Hans-Peter Buchstaller, Griesheim (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 14/420,578

(22) PCT Filed: Jul. 12, 2013

(86) PCT No.: PCT/EP2013/002085
§ 371 (c)(1),
(2) Date: Feb. 9, 2015

(87) PCT Pub. No.: WO2014/023390
PCT Pub. Date: Feb. 13, 2014

(65) Prior Publication Data
US 2015/0210686 A1    Jul. 30, 2015

(30) Foreign Application Priority Data
Aug. 8, 2012   (EP) .................................... 12005752

(51) Int. Cl.
| | | |
|---|---|---|
| C07D 217/24 | (2006.01) | |
| C07D 471/04 | (2006.01) | |
| A61K 31/472 | (2006.01) | |
| C07D 401/10 | (2006.01) | |
| C07D 405/10 | (2006.01) | |
| A61K 31/4375 | (2006.01) | |
| A61K 31/4725 | (2006.01) | |

(52) U.S. Cl.
CPC .......... *C07D 471/04* (2013.01); *A61K 31/4375* (2013.01); *A61K 31/472* (2013.01); *A61K 31/4725* (2013.01); *C07D 217/24* (2013.01); *C07D 401/10* (2013.01); *C07D 405/10* (2013.01)

(58) Field of Classification Search
None
See application file for complete search history.

(56) References Cited

U.S. PATENT DOCUMENTS

| | | | |
|---|---|---|---|
| 6,790,844 B2 | 9/2004 | Ueno et al. | |
| 6,995,174 B2 | 2/2006 | Wang et al. | |
| 7,449,479 B2 | 11/2008 | Wang et al. | |
| 7,772,180 B2 | 8/2010 | Sin et al. | |
| 7,915,291 B2 | 3/2011 | Wang et al. | |
| 8,053,440 B2 | 11/2011 | Hansen et al. | |
| 8,299,094 B2 | 10/2012 | Wang et al. | |
| 8,507,722 B2 | 8/2013 | Wang et al. | |
| 8,710,229 B2 | 4/2014 | Wang et al. | |
| 8,883,763 B2 | 11/2014 | Popov et al. | |
| 8,889,698 B2 | 11/2014 | Hansen et al. | |
| 8,889,871 B2 | 11/2014 | Wang et al. | |
| 2002/0013460 A1 | 1/2002 | Ueno et al. | |
| 2004/0106559 A1 | 6/2004 | Wang et al. | |
| 2006/0172950 A1 | 8/2006 | Wang et al. | |
| 2008/0119461 A1 | 5/2008 | Sin et al. | |
| 2008/0188467 A1 | 8/2008 | Wong et al. | |
| 2009/0274656 A1 | 11/2009 | Wang et al. | |
| 2013/0311482 A1 | 12/2011 | Wang et al. | |
| 2012/0015905 A1 | 1/2012 | Hansen | |
| 2012/0330019 A1 | 12/2012 | Wang et al. | |
| 2013/0096083 A1 | 4/2013 | Popov et al. | |
| 2013/0115190 A1 | 5/2013 | Hiebert et al. | |
| 2013/0267713 A1 | 10/2013 | Wang et al. | |
| 2014/0163231 A1 | 6/2014 | Wang et al. | |
| 2015/0005342 A1 | 1/2015 | Wang et al. | |

FOREIGN PATENT DOCUMENTS

| | | |
|---|---|---|
| EP | 1020445 A1 | 7/2000 |
| WO | 9911622 A1 | 3/1999 |
| WO | 03099274 A1 | 12/2003 |
| WO | 2008060927 A2 | 5/2008 |
| WO | 2011107709 A1 | 9/2011 |
| WO | 2012151195 A1 | 11/2012 |
| WO | 2013132253 A1 | 9/2013 |

OTHER PUBLICATIONS

Houlihan et al, Journal of Medicinal Chemistry (1993), 36(21), pp. 3098-3102.*
International Search Report for PCT/EP2013/002085 dated Feb. 3, 2014.
Cho, W. et al., "Synthesis and biological evaluation of 3-arylisoquinolines as antitumor agents," Bioorganic & Medicinal Chemistry Letters, 1998, vol. 8, pp. 41-46.
Cheon, S. H. et al., "Structure-Activity Relationship Studies of Isoquinolinone Type Anticancer Agent," Arch Pharm Res, 2001, vol. 24, No. 4, pp. 276-280.

(Continued)

*Primary Examiner* — Zinna Northington Davis
(74) *Attorney, Agent, or Firm* — Millen, White, Zelano & Branigan, P.C.

(57) ABSTRACT

Compounds of the formula I

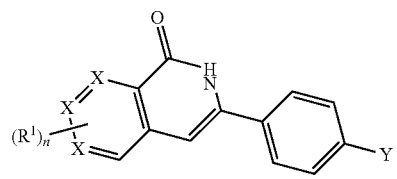

in which $R^1$, X, Y and n have the meanings indicated in claim 1, are inhibitors of Tankyrase, and can be employed, inter alia, for the treatment of diseases such as cancer, cardiovascular diseases, central nervous system injury and different forms of inflammation.

4 Claims, No Drawings

(56) References Cited

OTHER PUBLICATIONS

Olbrich, G. et al., "CNDO/S-CI calculations of some carbonyl-containing organic luminophores with a stilbene subchromophore," Database HCaplus, 1985, vol. 40, No. 8, pp. 856-863.

Sarkhel, B. K. et al., "Synthesis of Some 3-Aryl-5-methoxy-7-methylisocoumarins," Indian J. Chem., Nov. 1978, vol. 16B.

Rose, A. et al., "Oxygen Heterocycles. Part XIII. From 3-Arylisocoumarins to 3-Aryl-isoquinolines and 4-Aryl-5H-2,3-benzodiazepines," Journal of the Chemical Society, Section C: Organic Chemistry, Chemistry Society, 1968, pp. 2205-2208.

Hattori, K. et al., "Preparation of 2H-isoquinolin-1-one derivatives and use thereof as anticancer agents," Aug. 15, 2005, XP002715451.

* cited by examiner

(AZA-)ISOQUINOLINONE DERIVATIVES

BACKGROUND OF THE INVENTION

The invention had the object of finding novel compounds having valuable properties, in particular those which can be used for the preparation of medicaments.

The present invention relates to bicyclic pyrazinone derivatives which inhibit the activity of Tankyrases (TANKs) and poly(ADP-ribose)polymerase PARP-1. The compounds of this invention are therefore useful in treating diseases such as cancer, multiple sclerosis, cardiovascular diseases, central nervous system injury and different forms of inflammation. The present invention also provides methods for preparing these compounds, pharmaceutical compositions comprising these compounds, and methods of treating diseases utilizing pharmaceutical compositions comprising these compounds.

The nuclear enzyme poly(ADP-ribose) polymerase-1 (PARP-1) is a member of the PARP enzyme family. This growing family of enzymes consist of PARPs such as, for example: PARP-1, PARP-2, PARP-3 and Vault-PARP; and Tankyrases (TANKs), such as, for example: TANK-1 and TANK-2. PARP is also referred to as poly(adenosine 5'-diphospho-ribose) polymerase or PARS (poly(ADP-ribose) synthetase).

TANK-1 seems to be required for the polymerization of mitotic spindle-associated poly(ADP-ribose). The poly (ADP-ribosyl)ation activity of TANK-1 might be crucial for the accurate formation and maintenance of spindle bipolarity. Furthermore, PARP activity of TANK-1 has been shown to be required for normal telomere separation before anaphase. Interference with tankyrase PARP activity results in aberrant mitosis, which engenders a transient cell cycle arrest, probably due to spindle checkpoint activation, followed by cell death. Inhibition of tankyrases is therefore expected to have a cytotoxic effect on proliferating tumor cells (WO 2008/107478).

PARP inhibitors are described by M. Rouleau et al. in Nature Reviews, Volume 10, 293-301 in clinical cancer studies (Table 2, page 298).

According to a review by Horvath and Szabo (Drug News Perspect 20(3), April 2007, 171-181) most recent studies demonstrated that PARP inhibitors enhance the cancer cell death primarily because they interfere with DNA repair on various levels. More recent studies have also demonstrated that PARP inhibitors inhibit angiogenesis, either by inhibiting growth factor expression, or by inhibiting growth factor-induced cellular proliferative responses. These findings might also have implications on the mode of PARP inhibitors' anti-cancer effects in vivo.

Also a study by Tentori et al. (Eur. J. Cancer, 2007, 43 (14) 2124-2133) shows that PARP inhibitors abrogate VEGF or placental growth factor-induced migration and prevent formation of tubule-like networks in cell-based systems, and impair angiogenesis in vivo. The study also demonstrates that growth factor-induced angiogenesis is deficient in PARP-1 knock-out mice. The results of the study provide evidence for targeting PARP for anti-angiogenesis, adding novel therapeutic implications to the use of PARP inhibitors in cancer treatment.

Defects in conserved signaling pathways are well known to play key roles in the origins and behavior of essentially all cancers (E. A. Fearon, Cancer Cell, Vol. 16, issue 5, 2009, 366-368). The Wnt pathway is a target for anti-cancer therapy. A key feature of the Wnt pathway is the regulated proteolysis (degradation) of β-catenin by the β-catenin destruction complex. Proteins like WTX, APC or Axin are involved in the degradation process. A proper degradation of β-catenin is important to avoid an inappropriate activation of the Wnt pathway which has been observed in many cancers. Tankyrases inhibit activity of Axin and hence inhibit the degradation of β-catenin.

Consequently, tankyrase inhibitors increase degradation of β-catenin. A recent paper in the journal Nature not only offers important new insights into proteins regulating Wnt signaling but also further supports the approach to antagonize β-catenin levels and localization via small molecules (Huang et al., 2009; Nature, Vol 461, 614-620). The compound XAV939 inhibits growth of DLD-1-cancer cells. They found that XAV9393 blocked Wnt-stimulated accumulation of β-catenin by increasing the levels of the AXIN1 and AXIN2 proteins. Subsequent work by the authors established that XAV939 regulates AXIN levels via inhibition of tankyrases 1 and 2 (TNKS1 and TNKS2), both of which are members of the poly(ADP-ribose) polymerase (PARP) protein family (S. J. Hsiao et al., Biochimie 90, 2008, 83-92).

It has been found that the compounds according to the invention and salts thereof have very valuable pharmacological properties while being well tolerated.

The present invention specifically relates to compounds of the formula I which inhibit Tankyrase 1 and 2, to compositions which comprise these compounds, and to processes for the use thereof for the treatment of TANK-induced diseases and complaints.

The compounds of the formula I can furthermore be used for the isolation and investigation of the activity or expression of TANKs. In addition, they are particularly suitable for use in diagnostic methods for diseases in connection with unregulated or disturbed TANK activity.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

The susceptibility of a particular cell to treatment with the compounds according to the invention can be determined by in vitro tests. Typically, a culture of the cell is combined with a compound according to the invention at various concentrations for a period of time which is sufficient to allow active agents such as anti IgM to induce a cellular response such as expression of a surface marker, usually between about one hour and one week. In vitro testing can be carried out using cultivated cells from blood or from a biopsy sample. The amount of surface marker expressed is assessed by flow cytometry using specific antibodies recognising the marker.

The dose varies depending on the specific compound used, the specific disease, the patient status, etc. A therapeutic dose is typically sufficient considerably to reduce the undesired cell population in the target tissue while the viability of the patient is maintained. The treatment is generally continued until a considerable reduction has occurred, for example an at least about 50% reduction in the cell burden, and may be continued until essentially no more undesired cells are detected in the body.

PRIOR ART

Other (aza-)isoquinolinone derivatives are described as intermediates in EP 1020445. Other isoquinolinone derivatives are described as PARP inhibitors in WO 2010/133647.

Other isoquinolinone derivatives are described by:
Won-Jea Cho et al, Bioorganic and Medicinal Chemistry Letters (1998), 8, 41-46;
Sung Hoon Cheon et al, Archives of Pharmacal Research (1997), 20, 138-143
Sung Hoon Cheon et al, Archives of Pharmacal Research (2001), 24, 276-280.
A quinazolinone derivative is described as tankyrase inhibitor by E. Wahlberg et al., Nature Biotechnology (2012), 30(3), 283.

SUMMARY OF THE INVENTION

The invention relates to compounds of the formula I

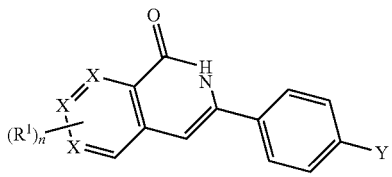

in which
$R^1$ denotes F, Cl, $CH_3$, $OCH_3$, $CF_3$, $CHF_2$ or $CH_2F$,
$R^2$ denotes H or unbranched or branched alkyl with 1-6 C-atoms,
X denotes C or N, with the proviso that only one X denotes N,
Y denotes A, Cyc, $[C(R^2)_2]_qOA$, $[C(R^2)_2]_qN(R^2)_2$, $[C(R^2)_2]_pHet^1$, $[C(R^2)_2]_pCOOR^2$, $[C(R^2)_2]_pCON(R^2)_2$ or $[C(R^2)_2]_pSO_2N(R^2)_2$,
Ar denotes phenyl, which is unsubstituted, or mono- or disubstituted by Hal, A, $[C(R^2)_2]_pOR^2$, $[C(R^2)_2]_pN(R^2)_2$, $[C(R^2)_2]_pHet^2$, $NO_2$, CN, $[C(R^2)_2]_pCOOR$, $[C(R^2)_2]_pN(R^2)_2$, $N(R^2)_2COA$, $NR^2SO_2A$, $[C(R^2)_2]_pSO_2N(R^2)_2$, $S(O)_nA$, $COHet^2$, $O[C(R^2)_2]_pN(R^2)_2$, $O[C(R^2)_2]_pHet^2$, NHCOOA, $NHCON(R^2)_2$ or COA,
$Het^1$ denotes pyrrolidinyl, azetidinyl, tetrahydroimidazolyl, tetrahydrofuranyl, oxetanyl, tetrahydropyrazolyl, tetrahydropyranyl, piperidinyl, morpholinyl, hexahydropyridazinyl, hexahydropyrimidinyl, [1,3]dioxolanyl, piperazinyl, furyl, thienyl, pyrrolyl, imidazolyl, pyrazolyl, oxazolyl, isoxazolyl, oxadiazolyl, thiazolyl, triazolyl, tetrazolyl, pyridyl, pyrimidyl, pyridazinyl, indolyl, isoindolyl, benzimidazolyl, indazolyl, quinolyl, 1,3-benzodioxolyl, benzothiophenyl, benzofuranyl, imidazopyridyl or furo[3,2-b]pyridyl, each of which is unsubstituted or mono- or disubstituted by Hal, A, $[C(R^2)_2]_pOR^2$, $[C(R^2)_2]_pN(R^2)_2$, $[C(R^2)_2]_pHet^2$, $[C(R^2)_2]_pOHet^2$ $[C(R^2)_2]_pAr$, $NO_2$, CN, $[C(R^2)_2]_pCOOR^2$, $[C(R^2)_2]_pCON(R^2)_2$, $NR^2COA$, $NR^2SO_2A$, $[C(R^2)_2]_pSO_2N(R^2)_2$, $S(O)_nA$, $COHet^2$, $O[C(R^2)_2]_mN(R^2)_2$, $O[C(R^2)_2]_pAr$, $O[C(R^2)_2]_pHet^2$, NHCOOA, $NHCON(R^2)_2$, CHO, COA, =S, =NR and/or =O,
$Het^2$ denotes dihydropyrrolyl, pyrrolidinyl, azetidinyl, oxetanyl, tetrahydroimidazolyl, dihydropyrazolyl, tetrahydropyrazolyl, tetrahydrofuranyl, dihydropyridyl, tetrahydropyridyl, piperidinyl, morpholinyl, hexahydropyridazinyl, hexahydropyrimidinyl, [1,3]dioxolanyl, tetrahydropyranyl or piperazinyl, each of which is unsubstituted or mono- or disubstituted by Hal, CN, $OR^2$, $COOR^2$, $CON(R^2)_2$, $S(O)_nA$, $S(O)_nAr$, COA, A and/or =O,
A denotes unbranched or branched alkyl with 1-10 C-atoms, wherein two adjacent carbon atoms may form a double bond and/or one or two non-adjacent CH— and/or $CH_2$- groups may be replaced by N—, O— and/or S-atoms and wherein 1-7 H-atoms may be replaced by F or Cl,
Cyc denotes cycloalkyl with 3-7 C-atoms, which is unsubstituted or monosubstituted by OH, Hal or A,
Hal denotes F, Cl, Br or I,
n denotes 0, 1 or 2,
m denotes 1, 2 or 3,
p denotes 0, 1, 2, 3 or 4,
q denotes 1, 2, 3 or 4,
with the proviso that, if $R^1$ is absent or methyl or methoxy, then Y is not methyl, trifluoromethyl, piperidinomethyl, butyl, 3-methoxy-1-propyl or 4-morpholinyl,
and pharmaceutically acceptable solvates, salts, tautomers and stereoisomers thereof, including mixtures thereof in all ratios.

The invention also relates to the optically active forms (stereoisomers), the enantiomers, the racemates, the diastereomers and the hydrates and solvates of these compounds.

The invention relates to compounds of formula I and their tautomers of formula Ia

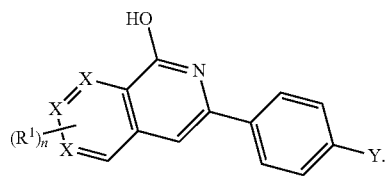

Moreover, the invention relates to pharmaceutically acceptable derivatives of compounds of formula I.

The term solvates of the compounds is taken to mean adductions of inert solvent molecules onto the compounds which form owing to their mutual attractive force. Solvates are, for example, mono- or dihydrates or alkoxides.

It is understood, that the invention also relates to the solvates of the salts. The term pharmaceutically acceptable derivatives is taken to mean, for example, the salts of the compounds according to the invention and also so-called prodrug compounds.

As used herein and unless otherwise indicated, the term "prodrug" means a derivative of a compound of formula I that can hydrolyze, oxidize, or otherwise react under biological conditions (in vitro or in vivo) to provide an active compound, particularly a compound of formula I. Examples of prodrugs include, but are not limited to, derivatives and metabolites of a compound of formula I that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. In certain embodiments, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers Gmfh).

The expression "effective amount" denotes the amount of a medicament or of a pharmaceutical active ingredient which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence:
improved treatment, healing, prevention or elimination of a disease, syndrome, condition, complaint, disorder or side-effects or also the reduction in the advance of a disease, complaint or disorder.

The expression "therapeutically effective amount" also encompasses the amounts which are effective for increasing normal physiological function.

The invention also relates to the use of mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution.

The invention relates to the compounds of the formula I and salts thereof and to a process for the preparation of compounds of the formula I and pharmaceutically acceptable salts, solvates, tautomers and stereoisomers thereof, characterised in that
a) a compound of the formula II

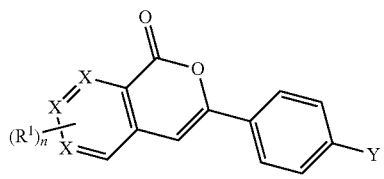

in which $R^1$, X, Y and n have the meanings indicated in claim 1, is reacted with $NH_3$,
or
b) a radical Y is converted into another radical Y by
i) converting a halogen atom into an ester group,
ii) converting an ester group into an alcohol group,
iii) converting in a Suzuki coupling a halogenated phenyl ring into an arylated phenyl ring,
and/or
a base or acid of the formula I is converted into one of its salts.

Above and below, the radicals $R^1$, X, Y and n have the meanings indicated for the formula I, unless expressly stated otherwise.

A denotes alkyl, this is unbranched (linear) or branched, and has 1, 2, 3, 4, 5, 6, 7, 8, 9 or 10 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1- , 1,2- or 2,2-dimethylpropyl, 1-ethyl-propyl, hexyl, 1-, 2-, 3- or 4-methylpentyl, 1,1- , 1,2- , 1,3- , 2,2- , 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl.

A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl.

Moreover, A denotes preferably $CH_2OCH_3$, $CH_2CH_2OH$ or $CH_2CH_2OCH_3$. Cyc denotes cyclopropyl, cyclobutyl, cyclopentyl, cyclohexyl or cycloheptyl, preferably unsubstituted or monosubstituted by OH, Hal or A.

$R^1$ particularly preferably denotes H, F, Cl, $CH_3$, $OCH_3$ or $CF_3$.

$R^2$ preferably denotes H, methyl, ethyl, propyl, isopropyl, butyl, pentyl or hexyl, particularly preferably H or methyl.

Ar denotes preferably o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methylamino)phenyl, o-, m- or p-(N-methylaminocarbonyl)-phenyl, o-, m- or p-methoxyphenyl, o-, m- or p-ethoxyphenyl, o-, m- or p-ethoxycarbonylphenyl, o-, m- or p-(N,N-dimethylamino)phenyl, o-, m- or p-(N,N-dimethylaminocarbonyl)phenyl, o-, m- or p-(N-ethylamino)phenyl, o-, m- or p-(N,N-diethylamino)phenyl, o-, m- or p-fluorophenyl, o-, m- or p-bromophenyl, o-, m- or p-chlorophenyl, o-, m- or p-(methylsulfonamido)-phenyl, o-, m- or p-(methylsulfonyl)phenyl, o-, m- or p-cyanophenyl, o-, m- or p-carboxyphenyl, o-, m- or p-methoxycarbonylphenyl, o-, m- or p-formylphenyl, o-, m- or p-acetylphenyl, o-, m- or p-aminosulfonylphenyl, o-, m- or p-[2-(morpholin-4-yl)ethoxy]phenyl, o-, m- or p-[3-(N,N-diethyl-amino)propoxy]phenyl, furthermore preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-di-chloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl.

Ar furthermore preferably denotes phenyl, which is monosubstituted by Hal, A, $[C(R^2)_2]_p Het^2$ or $[C(R^2)_2]_p COOR^2$.

$Het^1$ preferably denotes pyrrolidinyl, azetidinyl, tetrahydroimidazolyl, tetrahydrofuranyl, tetrahydropyrazolyl, tetrahydropyranyl, piperidinyl, morpholinyl, hexahydropyridazinyl, hexahydropyrimidinyl, [1,3]dioxolanyl, piperazinyl, furyl, thienyl, pyrrolyl, imidazolyl, pyrazolyl, oxazolyl, isoxazolyl, oxadiazolyl, thiazolyl, triazolyl, tetrazolyl, pyridyl, pyrimidyl, pyridazinyl, indolyl, isoindolyl, benzimidazolyl, indazolyl, quinolyl, 1,3-benzodioxolyl, benzothiophenyl, benzofuranyl, imidazopyridyl or furo[3,2-b]pyridyl, each of which is unsubstituted or mono- or disubstituted by A and/or $[C(R^2)_2]_p OR^2$.

$Het^1$ particularly preferably denotes pyrrolidinyl, piperidinyl, tetrahydrofuranyl, oxetanyl or pyrazolyl, each of which is unsubstituted or monosubstituted by A or $[C(R^2)_2]_p OR^2$.

$Het^2$ particularly preferably denotes pyrrolidinyl, piperidinyl or pyrazolyl, each of which is monosubstituted by A.

Hal preferably denotes F, Cl or Br, but also I, particularly preferably F or Cl.

Throughout the invention, all radicals which occur more than once may be identical or different, i.e. are independent of one another.

The compounds of the formula I may have one or more chiral centres and can therefore occur in various stereoisomeric forms. The formula I encompasses all these forms.

Accordingly, the invention relates, in particular, to the compounds of the formula I in which at least one of the said radicals has one of the preferred meanings indicated above. Some preferred groups of compounds may be expressed by the following sub-formulae Ia to Id, which conform to the formula I and in which the radicals not designated in greater detail have the meaning indicated for the formula I, but in which in Ia Ar denotes phenyl, which is monosubstituted by Hal, A, $[C(R^2)_2]_p Het^2$ or $[C(R^2)_2]_p COOR^2$;

in Ib $Het^1$ denotes pyrrolidinyl, azetidinyl, tetrahydroimidazolyl, tetrahydrofuranyl, tetrahydropyrazolyl, tetrahydropyranyl, piperidinyl, morpholinyl, hexahydropyridazinyl, hexahydropyrimidinyl, [1,3]dioxolanyl, piperazinyl, furyl, thienyl, pyrrolyl, imidazolyl, pyrazolyl, oxazolyl, isoxazolyl, oxadiazolyl, thiazolyl, triazolyl, tetrazolyl, pyridyl, pyrimidyl, pyridazinyl, indolyl, isoindolyl, benzimidazolyl, indazolyl, quinolyl, 1,3-benzodioxolyl, benzothiophenyl, benzofuranyl, imidazopyridyl or furo[3,2-b]pyridyl, each of which is unsubstituted or mono- or disubstituted by A and/or $[C(R^2)_2]_p OR^2$;

in Ic $Het^2$ denotes pyrrolidinyl, piperidinyl or pyrazolyl, each of which is monosubstituted by A;

in Id $R^1$ denotes F, Cl, $CH_3$, $OCH_3$, $CF_3$, $CHF_2$ or $CH_2F$, $R^2$ denotes H or unbranched or branched alkyl with 1-6 C-atoms, X denotes C or N, with the proviso that only one X denotes N, Y denotes A, Cyc, $[C(R^2)_2]_q OA$, $[C(R^2)_2]_q N(R^2)_2$, $[C(R^2)_2]_p Het^1$, $[C(R^2)_2]_p COOR^2$, $[C(R^2)_2]_p CON(R^2)_2$ or $[C(R^2)_2]_p SO_2N(R^2)_2$, $Het^1$ denotes pyrrolidinyl, azetidinyl, tetrahydroimidazolyl, tetrahydrofuranyl, oxetanyl, tetrahydropyrazolyl, tetrahydropyranyl, piperidinyl, morpholinyl, hexahydropyridazinyl, hexahydropyrimidinyl, [1,3]dioxolanyl, piperazinyl, furyl, thienyl, pyrrolyl, imidazolyl, pyrazolyl, oxazolyl, isoxazolyl, oxadiazolyl, thiazolyl, triazolyl, tetrazolyl, pyridyl, pyrimidyl, pyridazinyl, indolyl, isoindolyl, benzimidazolyl, indazolyl, quinolyl, 1,3-benzodioxolyl, benzothiophenyl, benzofuranyl, imidazopyridyl or furo[3,2-b]pyridyl, each of which is unsubstituted or mono- or disubstituted by A and/or $[C(R^2)_2]_p OR^2$, A denotes unbranched or branched alkyl with 1-10 C-atoms, wherein two adjacent carbon atoms may form a double bond and/or one or two non-adjacent CH— and/or $CH_2$— groups may be replaced by N-atoms and wherein 1-7 H-atoms may be replaced by F or Cl, Cyc denotes cycloalkyl with 3-7 C-atoms, which is unsubstituted or monosubstituted by OH, Hal or A, n denotes 0, 1 or 2, p denotes 0, 1, 2, 3 or 4, q denotes 1, 2, 3 or 4, with the proviso that, if $R^1$ is absent or methyl or methoxy, then Y is not methyl, trifluoromethyl, piperidinomethyl, butyl, 3-methoxy-1-propyl or 4-morpholinyl, and pharmaceutically acceptable salts, solvates, tautomers and stereoisomers thereof, including mixtures thereof in all ratios.

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail.

The starting compounds of the formula II are generally known. If they are novel, however, they can be prepared by methods known per se.

Compounds of the formula I can preferably be obtained by reacting a compound of the formula II with $NH_3$.

Depending on the conditions used, the reaction time is between a few minutes and 14 days, the reaction temperature is between about −10° and 140°, normally between 30° and 130°, in particular between about 60° and about 120°. The reaction is carried out in an inert solvent.

Examples of suitable inert solvents are hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Particular preference is given to DMF.

Compounds of the formula I can furthermore be obtained by converting a radical Y into another radical Y by i) converting a halogen atom into an ester group,
ii) converting an ester group into an alcohol group,
iii) converting in a Suzuki coupling a halogenated phenyl ring into an arylated phenyl ring.

Step i):

Converting a halogen atom into an ester group preferably is carried out with carbon monoxide, preferably in an organic solvent; preferably in methanol and toluene under standard conditions.

Preferably the reaction is carried out under pressure, preferably 2-4 bar.

Preferably a palladium- and/or iron-complex are added, preferred complexes are (1,1'-bis(diphenylphosphino)-ferrocene)dichloropalladium(II) or 1,1'-bis(diphenylphosphino)-ferrocene. Depending on the conditions used, the reaction time is between a few minutes and 14 days, the reaction temperature is between about 40° and 140°, normally between 60° and 130°, in particular between about 90° and about 110°.

Step ii):

Converting an ester group into an alcohol group, preferably is carried out in presence of Cerium(III) chloride with an alkylmagnesiumchloride in THF under standard conditions or with lithiumaluminiumhydride in THF.

Step iii):

Converting a halogenated phenyl ring into an arylated phenyl ring, is carried out under standard conditions for a Suzuki coupling.

Step iv):

Converting a halogenated alkyl group into an alkyl group preferably is carried out with $LiAlH_4$ in THF or with zinc in acetic acid under standard conditions Esters can be saponified, for example, using acetic acid or using NaOH or KOH in water, water/THF or water/dioxane, at temperatures between 0 and 100°.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogen-phosphate, dinitrobenzoate, dodecylsulfate, ethanesulfonate, fumarate, formate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-(hydroxymethyl)methylamine (tromethamine), but this is not intended to represent a restriction.

Compounds of the present invention which contain basic nitrogen-containing groups can be quaternised using agents such as ($C_1$-$C_4$)alkyl halides, for example methyl, ethyl, isopropyl and tert-butyl chloride, bromide and iodide; di($C_1$-$C_4$) alkyl sulfates, for example dimethyl, diethyl and diamyl sulfate; ($C_{10}$-$C_{18}$)alkyl halides, for example decyl, dodecyl, lauryl, myristyl and stearyl chloride, bromide and iodide; and aryl($C_1$-$C_4$)alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

Particular preference is given to hydrochloride, dihydrochloride, hydrobromide, maleate, mesylate, phosphate, sulfate and succinate.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound of the formula I in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Isotopes

There is furthermore intended that a compound of the formula I includes isotope-labelled forms thereof. An isotope-labelled form of a compound of the formula I is identical to this compound apart from the fact that one or more atoms of the compound have been replaced by an atom or atoms having an atomic mass or mass number which differs from the atomic mass or mass number of the atom which usually occurs naturally. Exam-pies of isotopes which are readily commercially available and which can be incorporated into a compound of the formula I by well-known methods include isotopes of hydrogen, carbon, nitrogen, oxygen, phos-phorus, fluo-rine and chlorine, for example $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. A compound of the formula I, a prodrug, thereof or a pharmaceutically acceptable salt of either which contains one or more of the above-mentioned isotopes and/or other iso-topes of other atoms is intended to be part of the present invention. An isotope-labelled compound of the formula I can be used in a number of beneficial ways. For example, an isotope-labelled compound of the formula I into which, for example, a radio-isotope, such as $^3H$ or $^{14}C$, has been incorporated is suitable for medicament and/or substrate tissue distribution assays. These radioisotopes, i.e. tritium ($^3H$) and carbon-14 ($^{14}C$), are particularly preferred owing to simple preparation and excellent detectability. Incor-po-ra-tion of heavier isotopes, for example deuterium ($^2H$), into a compound of the formula I has therapeutic advantages owing to the higher metabolic stability of this isotope-labelled compound. Higher metabolic stability translates directly into an increased in vivo half-life or lower dosages, which under most circumstances would represent a preferred embodi-ment of the present invention. An isotope-labelled compound of the formula I can usually be prepared by carrying out the procedures dis-closed in the synthesis schemes and the related description, in the example part and in the preparation part in the present text, replacing a non-isotope-labelled reactant by a readily available isotope-labelled reactant.

Deuterium ($^2H$) can also be incorporated into a compound of the formula I for the purpose in order to manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus cause a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D=2\text{-}7$ are typical. If this rate difference is successfully applied to a com-pound of the formula I that is susceptible to oxidation, the profile of this compound in vivo can be drastically modified and result in improved pharmacokinetic properties.

When discovering and developing therapeutic agents, the person skilled in the art attempts to optimise pharmacokinetic parameters while retaining desirable in vitro properties. It is reasonable to assume that many com-pounds with poor pharmacokinetic profiles are susceptible to oxidative metabolism. In vitro liver microsomal assays currently available provide valuable information on the course of oxidative metabolism of this type, which in turn permits the rational design of deuterated compounds of the formula I with improved stability through resistance to such oxidative meta-bolism. Significant improvements in the pharmacokinetic profiles of compounds of the formula I are thereby obtained, and can be expressed quantitatively in terms of increases in the in vivo half-life (t/2), concen-tra-tion at maximum therapeutic effect ($C_{max}$), area under the dose response curve (AUC), and F; and in terms of reduced clearance, dose and materi-als costs.

The following is intended to illustrate the above: a compound of the formula I which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favourable and accurate determination of the extent of the extent to which the improve-ment in resistance to oxidative metabolism has improved. In this way, it is deter-mined that the half-life of the parent compound can be extended by up to 100% as the result of deuterium-hydrogen exchange of this type.

Deuterium-hydrogen exchange in a compound of the formula I can also be used to achieve a favourable modification of the metabolite spectrum of the starting compound in order to diminish or eliminate undesired toxic metabolites. For example, if a toxic metabolite arises through oxidative car-bon-hydrogen (C—H) bond cleavage, it can reasonably be assumed that the deuterated analogue will greatly diminish or eliminate production of the unwanted metabolite, even if the particular oxidation is not a rate-determining step. Further information on the state of the art with respect to deuterium-hydrogen exchange may be found, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33(10) 2927-2937, 1994, and Jarman et al. Carcinogenesis 16(4), 683-688, 1993.

The invention furthermore relates to medicaments comprising at least one compound of the formula I and/or pharmaceutically acceptable derivatives, solvates and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active ingredient per dosage unit.

Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tabletting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula I and salts, solvates and physiologically functional derivatives thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula I and the salts, solvates and physiologically functional derivatives thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I depends on a number of factors, including, for example, the age and weight of the animal, the precise condition that requires treatment, and its severity, the nature of the formulation and the method of administration, and is ultimately determined by the treating doctor or vet. However, an effective amount of a compound according to the invention is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

A combined treatment of this type can be achieved with the aid of simultaneous, consecutive or separate dispensing of the individual components of the treatment. Combination products of this type employ the compounds according to the invention.

The invention furthermore relates to medicaments comprising at least one compound of the formula I and/or pharmaceutically acceptable salts, solvates and stereoisomers thereof, including mixtures thereof in all ratios, and at least one further medicament active ingredient.

The invention also relates to a set (kit) consisting of separate packs of (a) an effective amount of a compound of the formula I and/or pharmaceutically acceptable salts, solvates and stereoisomers thereof, including mixtures thereof in all ratios, and
(b) an effective amount of a further medicament active ingredient.

The set comprises suitable containers, such as boxes, individual bottles, bags or ampoules. The set may, for example, comprise separate ampoules, each containing an effective amount of a compound of the formula I and/or pharmaceutically acceptable salts, solvates and stereoisomers thereof, including mixtures thereof in all ratios, and an effective amount of a further medicament active ingredient in dissolved or lyophilised form.

"Treating" as used herein, means an alleviation, in whole or in part, of symptoms associated with a disorder or disease, or slowing, or halting of further progression or worsening of those symptoms, or prevention or prophylaxis of the disease or disorder in a subject at risk for developing the disease or disorder.

The term "effective amount" in connection with a compound of formula (I) can mean an amount capable of alleviating, in whole or in part, symptoms associated with a disorder or disease, or slowing or halting further progression or worsening of those symptoms, or preventing or providing prophylaxis for the disease or disorder in a subject having or at risk for developing a disease disclosed herein, such as inflammatory conditions, immunological conditions, cancer or metabolic conditions.

In one embodiment an effective amount of a compound of formula (I) is an amount that inhibits a tankyrase in a cell, such as, for example, in vitro or in vivo. In some embodiments, the effective amount of the compound of formula (I) inhibits tankyrase in a cell by 10%, 20%, 30%, 40%, 50%, 60%, 70%, 80%, 90% or 99%, compared to the activity of tankyrase in an untreated cell. The effective amount of the compound of formula (I), for example in a pharmaceutical composition, may be at a level that will exercise the desired effect; for example, about 0.005 mg/kg of a subject's body weight to about 10 mg/kg of a subject's body weight in unit dosage for both oral and parenteral administration.

Use

The present compounds are suitable as pharmaceutical active ingredients for mammals, especially for humans, in the treatment of cancer, multiple sclerosis, cardiovascular diseases, central nervous system injury and different forms of inflammation.

The present invention encompasses the use of the compounds of the formula I and/or physiologically acceptable salts and solvates thereof for the preparation of a medicament for the treatment or prevention of cancer, multiple sclerosis, cardiovascular diseases, central nervous system injury and different forms of inflammation.

Examples of inflammatory diseases include rheumatoid arthritis, psoriasis, contact dermatitis, delayed hypersensitivity reaction and the like.

Also encompassed is the use of the compounds of the formula I and/or physiologically acceptable salts and solvates thereof for the preparation of a medicament for the treatment or prevention of a tankyrase-induced disease or a tankyrase-induced condition in a mammal, in which to this method a therapeutically effective amount of a compound according to the invention is administered to a sick mammal in need of such treatment. The therapeutic amount varies according to the specific disease and can be determined by the person skilled in the art without undue effort.

The expression "tankyrase-induced diseases or conditions" refers to pathological conditions that depend on the activity of one or more tankyrases. Diseases associated with tankyrase activity include cancer, multiple sclerosis, cardiovascular diseases, central nervous system injury and different forms of inflammation.

The present invention specifically relates to compounds of the formula I and pharmaceutically acceptable salts, solvates, tautomers and stereoisomers thereof, including mixtures thereof in all ratios, for the use for the treatment of diseases in which the inhibition, regulation and/or modulation inhibition of tankyrase plays a role.

The present invention specifically relates to compounds of the formula I and pharmaceutically acceptable salts, solvates, tautomers and stereoisomers thereof, including mixtures thereof in all ratios, for the use for the inhibition of tankyrase.

The present invention specifically relates to compounds of the formula I and pharmaceutically acceptable salts, solvates, tautomers and stereoisomers thereof, including mixtures thereof in all ratios, for the use for the treatment of cancer, multiple sclerosis, cardiovascular diseases, central nervous system injury and different forms of inflammation.

The present invention specifically relates to methods for treating or preventing cancer, multiple sclerosis, cardiovascular diseases, central nervous system injury and different forms of inflammation, comprising administering to a subject in need thereof an effective amount of a compound of formula I or a pharmaceutically acceptable salt, tautomer, stereoisomer or solvate thereof.

Representative cancers that compounds of formula I are useful for treating or preventing include, but are not limited to, cancer of the head, neck, eye, mouth, throat, esophagus, bronchus, larynx, pharynx, chest, bone, lung, colon, rectum, stomach, prostate, urinary bladder, uterine, cervix, breast, ovaries, testicles or other reproductive organs, skin, thyroid, blood, lymph nodes, kidney, liver, pancreas, brain, central nervous system, solid tumors and blood-borne tumors.

Representative cardiovascular diseases that compounds of formula I are useful for treating or preventing include, but are not limited to, restenosis, atherosclerosis and its consequences such as stroke, myocardial infarction, ischemic damage to the heart, lung, gut, kidney, liver, pancreas, spleen or brain.

The present invention relates to a method of treating a proliferative, autoimmune, anti inflammatory or infectious disease disorder that comprises administering to a subject in need thereof a therapeutically effective amount of a compound of formula I.

Preferably, the present invention relates to a method wherein the disease is a cancer.

Particularly preferable, the present invention relates to a method wherein the disease is a cancer, wherein administration is simultaneous, sequential or in alternation with administration of at least one other active drug agent.

The disclosed compounds of the formula I can be administered in combination with other known therapeutic agents, including anticancer agents. As used here, the term "anticancer agent" relates to any agent which is administered to a patient with cancer for the purposes of treating the cancer.

The anti-cancer treatment defined herein may be applied as a sole therapy or may involve, in addition to the compound of the invention, conventional surgery or radiotherapy or chemotherapy. Such chemotherapy may include one or more of the following categories of anti-tumour agents:

(i) antiproliferative/antineoplastic/DNA-damaging agents and combinations thereof, as used in medical oncology, such as alkylating agents (for example cis-platin, carboplatin, cyclophosphamide, nitrogen mustard, melphalan, chloroambucil, busulphan and nitrosoureas); antimetabolites (for example antifolates such as fluoropyrimidines like 5-fluorouracil and tegafur, raltitrexed, methotrexate, cytosine arabinoside, hydroxyurea and gemcitabine); antitumour antibiotics (for example anthracyclines, like adriamycin, bleomycin, doxorubicin, daunomycin, epirubicin, idarubicin, mitomycin-C, dactinomycin and mithramycin); antimitotic agents (for example vinca alkaloids, like vincristine, vinblastine, vindesine and vinorelbine, and taxoids, like taxol and taxotere); topoisomerase inhibitors (for example epipodophyllotoxins, like etoposide and teniposide, amsacrine, topotecan, irinotecan and camptothecin) and cell-differentiating agents (for example all-trans-retinoic acid, 13-cis-retinoic acid and fenretinide);

(ii) cytostatic agents, such as antioestrogens (for example tamoxifen, toremifene, raloxifene, droloxifene and iodoxyfene), oestrogen receptor downregulators (for example fulvestrant), antiandrogens (for example bicalutamide, flutamide, nilutamide and cyproterone acetate), LHRH antagonists or LHRH agonists (for example goserelin, leuprorelin and buserelin), progesterones (for example megestrol acetate), aromatase inhibitors (for example as anastrozole, letrozole, vorazole and exemestane) and inhibitors of 5α-reductase, such as finasteride;

(iii) agents which inhibit cancer cell invasion (for example metalloproteinase inhibitors, like marimastat, and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbbl antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors, such as N-(3-chloro-4-fluorophenyl)-7-methoxy-6-(3-morpholinopropoxy)quinazolin-4-amine (gefitinib, AZD1839), N-(3-ethynyl-phenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033)), for example inhibitors of the platelet-derived growth factor family and for example inhibitors of the hepatocyte growth factor family;

(v) antiangiogenic agents, such as those which inhibit the effects of vascular endothelial growth factor, (for example the anti-vascular endothelial cell growth factor antibody bevacizumab [Avastin™], compounds such as those disclosed in published international patent applications WO 97/22596, WO 97/30035, WO 97/32856 and WO 98/13354) and compounds that work by other mechanisms (for example linomide, inhibitors of integrin αvβ3 function and angiostatin);

(vi) vessel-damaging agents, such as combretastatin A4 and compounds disclosed in international patent applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-Ras antisense;

(viii) gene therapy approaches, including, for example, approaches for replacement of aberrant genes, such as aberrant p53 or aberrant BRCA1 or BRCA2, GDEPT (gene-directed enzyme pro-drug therapy) approaches, such as those using cytosine deaminase, thymidine kinase or a bacterial nitroreductase enzyme, and approaches for increasing patient tolerance to chemotherapy or radiotherapy, such as multi-drug resistance gene therapy; and (ix) immunotherapy approaches, including, for example, ex-vivo and in-vivo approaches for increasing the immunogenicity of patient tumour cells, such as transfection with cytokines, such as interleukin 2, interleukin 4 or granulocyte-macrophage colony stimulating factor, approaches for decreasing T-cell anergy, approaches using transfected immune cells, such as cytokine-transfected dendritic cells, approaches using cytokine-transfected tumour cell lines, and approaches using anti-idiotypic antibodies.

The medicaments from Table 1 below are preferably, but not exclusively, combined with the compounds of the formula I.

TABLE 1

| | | |
|---|---|---|
| Alkylating agents | Cyclophosphamide | Lomustine |
| | Busulfan | Procarbazine |
| | Ifosfamide | Altretamine |
| | Melphalan | Estramustine phosphate |
| | Hexamethylmelamine | Mechloroethamine |
| | Thiotepa | Streptozocin |
| | chloroambucil | Temozolomide |
| | Dacarbazine | Semustine |
| | Carmustine | |
| Platinum agents | Cisplatin | Carboplatin |
| | Oxaliplatin | ZD-0473 (AnorMED) |
| | Spiroplatin | Lobaplatin (Aeterna) |
| | Carboxyphthalatoplatinum | Satraplatin (Johnson Matthey) |
| | Tetraplatin | BBR-3464 |
| | Ormiplatin | (Hoffmann-La Roche) |
| | Iproplatin | SM-11355 (Sumitomo) |
| | | AP-5280 (Access) |
| Antimetabolites | Azacytidine | Tomudex |
| | Gemcitabine | Trimetrexate |
| | Capecitabine | Deoxycoformycin |
| | 5-fluorouracil | Fludarabine |
| | Floxuridine | Pentostatin |
| | 2-chlorodesoxyadenosine | Raltitrexed |
| | 6-Mercaptopurine | Hydroxyurea |
| | 6-Thioguanine | Decitabine (SuperGen) |
| | Cytarabine | Clofarabine (Bioenvision) |
| | 2-fluorodesoxycytidine | Irofulven (MGI Pharma) |
| | Methotrexate | DMDC (Hoffmann-La Roche) |
| | Idatrexate | Ethynylcytidine (Taiho) |
| Topoisomerase inhibitors | Amsacrine | Rubitecan (SuperGen) |
| | Epirubicin | Exatecan mesylate (Daiichi) |
| | Etoposide | Quinamed (ChemGenex) |
| | Teniposide or mitoxantrone | Gimatecan (Sigma-Tau) |
| | Irinotecan (CPT-11) | Diflomotecan (Beaufour-Ipsen) |
| | 7-ethyl-10-hydroxycamptothecin | TAS-103 (Taiho) |
| | Topotecan | Elsamitrucin (Spectrum) |
| | Dexrazoxanet (TopoTarget) | J-107088 (Merck & Co) |
| | Pixantrone (Novuspharma) | BNP-1350 (BioNumerik) |
| | Rebeccamycin analogue (Exelixis) | CKD-602 (Chong Kun Dang) |
| | BBR-3576 (Novuspharma) | KW-2170 (Kyowa Hakko) |
| Antitumour antibiotics | Dactinomycin (Actinomycin D) | Amonafide |
| | Doxorubicin (Adriamycin) | Azonafide |
| | Deoxyrubicin | Anthrapyrazole |
| | Valrubicin | Oxantrazole |
| | Daunorubicin (Daunomycin) | Losoxantrone |
| | Epirubicin | Bleomycin sulfate (Blenoxan) |
| | Therarubicin | Bleomycinic acid |
| | Idarubicin | Bleomycin A |
| | Rubidazon | Bleomycin B |
| | Plicamycinp | Mitomycin C |
| | | MEN-10755 (Menarini) |

TABLE 1-continued

| | | |
|---|---|---|
| | Porfiromycin | GPX-100 (Gem Pharmaceuticals) |
| | Cyanomorpholinodoxo-rubicin | |
| | Mitoxantron (Novantron) | |
| Antimitotic agents | Paclitaxel | SB 408075 (GlaxoSmithKline) |
| | Docetaxel | |
| | Colchicine | E7010 (Abbott) |
| | Vinblastine | PG-TXL (Cell Therapeutics) |
| | Vincristine | |
| | Vinorelbine | IDN 5109 (Bayer) |
| | Vindesine | A 105972 (Abbott) |
| | Dolastatin 10 (NCI) | A 204197 (Abbott) |
| | Rhizoxin (Fujisawa) | LU 223651 (BASF) |
| | Mivobulin (Warner-Lambert) | D 24851 (ASTA Medica) |
| | | ER-86526 (Eisai) |
| | Cemadotin (BASF) | Combretastatin A4 (BMS) |
| | RPR 109881A (Aventis) | Isohomohalichondrin-B (PharmaMar) |
| | TXD 258 (Aventis) | |
| | Epothilone B (Novartis) | ZD 6126 (AstraZeneca) |
| | T 900607 (Tularik) | PEG-Paclitaxel (Enzon) |
| | T 138067 (Tularik) | AZ10992 (Asahi) |
| | Cryptophycin 52 (Eli Lilly) | !DN-5109 (Indena) |
| | Vinflunine (Fabre) | AVLB (Prescient NeuroPharma) |
| | Auristatin PE (Teikoku Hormone) | Azaepothilon B (BMS) |
| | BMS 247550 (BMS) | BNP- 7787 (BioNumerik) |
| | BMS 184476 (BMS) | CA-4-prodrug (OXiGENE) |
| | BMS 188797 (BMS) | Dolastatin-10 (NrH) |
| | Taxoprexin (Protarga) | CA-4 (OXiGENE) |
| Aromatase inhibitors | Aminoglutethimide | Exemestan |
| | Letrozole | Atamestan (BioMedicines) |
| | Anastrazole | YM-511 (Yamanouchi) |
| | Formestan | |
| Thymidylate synthase inhibitors | Pemetrexed (Eli Lilly) | Nolatrexed (Eximias) |
| | ZD-9331 (BTG) | CoFactor ™ (BioKeys) |
| DNA antagonists | Trabectedin (PharmaMar) | Mafosfamide (Baxter International) |
| | Glufosfamide (Baxter International) | Apaziquone (Spectrum Pharmaceuticals) |
| | Albumin + 32P (Isotope Solutions) | O6-benzylguanine (Paligent) |
| | Thymectacin (NewBiotics) | |
| | Edotreotid (Novartis) | |
| Farnesyl transferase inhibitors | Arglabin (NuOncology Labs) | Tipifarnib (Johnson & Johnson) |
| | lonafarnib (Schering-Plough) | Perillyl alcohol (DOR BioPharma) |
| | BAY-43-9006 (Bayer) | |
| Pump inhibitors | CBT-1 (CBA Pharma) | Zosuquidar trihydrochloride (Eli Lilly) |
| | Tariquidar (Xenova) | |
| | MS-209 (Schering AG) | Biricodar dicitrate (Vertex) |
| Histone acetyl transferase inhibitors | Tacedinaline (Pfizer) | Pivaloyloxymethyl butyrate (Titan) |
| | SAHA (Aton Pharma) | |
| | MS-275 (Schering AG) | Depsipeptide (Fujisawa) |
| Metalloproteinase inhibitors | Neovastat (Aeterna Laboratories) | CMT -3 (CollaGenex) |
| | Marimastat (British Biotech) | BMS-275291 (Celltech) |
| Ribonucleoside reductase inhibitors | Gallium maltolate (Titan) | Tezacitabine (Aventis) |
| | Triapin (Vion) | Didox (Molecules for Health) |
| TNF-alpha agonists/ antagonists | Virulizin (Lorus Therapeutics) | Revimid (Celgene) |
| | CDC-394 (Celgene) | |
| Endothelin-A receptor antagonists | Atrasentan (Abbot) | YM-598 (Yamanouchi) |
| | ZD-4054 (AstraZeneca) | |
| Retinoic acid receptor agonists | Fenretinide (Johnson & Johnson) | Alitretinoin (Ligand) |
| | LGD-1550 (Ligand) | |

TABLE 1-continued

| | | |
|---|---|---|
| Immunomodulators | Interferon<br>Oncophage (Antigenics)<br>GMK (Progenics)<br>Adenocarcinoma vaccine (Biomira)<br>CTP-37 (AVI BioPharma)<br>JRX-2 (Immuno-Rx)<br>PEP-005 (Peplin Biotech)<br>Synchrovax vaccines (CTL Immuno)<br>Melanoma vaccine (CTL Immuno)<br>p21-RAS vaccine (Gem-Vax) | Dexosome therapy (Anosys)<br>Pentrix (Australian Cancer Technology)<br>JSF-154 (Tragen)<br>Cancer vaccine (Intercell)<br>Norelin (Biostar)<br>BLP-25 (Biomira)<br>MGV (Progenics)<br>β-Alethin (Dovetail)<br>CLL-Thera (Vasogen) |
| Hormonal and antihormonal agents | Oestrogens<br>Conjugated oestrogens<br>Ethynyloestradiol<br>chlorotrianisene<br>Idenestrol<br>Hydroxyprogesterone caproate<br>Medroxyprogesterone<br>Testosterone<br>Testosterone propionate<br>Fluoxymesterone<br>Methyltestosterone<br>Diethylstilbestrol<br>Megestrol<br>Tamoxifen<br>Toremofin<br>Dexamethasone | Prednisone<br>Methylprednisolone<br>Prednisolone<br>Aminoglutethimide<br>Leuprolide<br>Goserelin<br>Leuporelin<br>Bicalutamide<br>Flutamide<br>Octreotide<br>Nilutamide<br>Mitotan<br>P-04 (Novogen)<br>2-Methoxyoestradiol (EntreMed)<br>Arzoxifen (Eli Lilly) |
| Photodynamic agents | Talaporfin (Light Sciences)<br>Theralux (Theratechnologies)<br>Motexafin-Gadolinium (Pharmacyclics) | Pd-Bacteriopheophorbid (Yeda)<br>Lutetium-Texaphyrin (Pharmacyclics)<br>Hypericin |
| Tyrosine kinase inhibitors | Imatinib (Novartis)<br>Leflunomide(Sugen/Pharmacia)<br>ZDI839 (AstraZeneca)<br>Erlotinib (Oncogene Science)<br>Canertjnib (Pfizer)<br>Squalamine (Genaera)<br>SU5416 (Pharmacia)<br>SU6668 (Pharmacia)<br>ZD4190 (AstraZeneca)<br>ZD6474 (AstraZeneca)<br>Vatalanib (Novartis)<br>PKI166 (Novartis)<br>GW2016 (GlaxoSmith-Kline)<br>EKB-509 (Wyeth)<br>EKB-569 (Wyeth) | Kahalide F (PharmaMar)<br>CEP-701 (Cephalon)<br>CEP-751 (Cephalon)<br>MLN518 (Millenium)<br>PKC412 (Novartis)<br>Phenoxodiol O<br>Trastuzumab (Genentech)<br>C225 (ImClone)<br>rhu-Mab (Genentech)<br>MDX-H210 (Medarex)<br>2C4 (Genentech)<br>MDX-447 (Medarex)<br>ABX-EGF (Abgenix)<br>IMC-1C11 (ImClone) |
| Various agents | SR-27897 (CCK-A inhibitor, Sanofi-Synthelabo)<br>Tocladesine (cyclic AMP agonist, Ribapharm)<br>Alvocidib (CDK inhibitor, Aventis)<br>CV-247 (COX-2 inhibitor, Ivy Medical)<br>P54 (COX-2 inhibitor, Phytopharm)<br>CapCell ™ (CYP450 stimulant, Bavarian Nordic)<br>GCS-IOO (gal3 antagonist, GlycoGenesys)<br>G17DT immunogen (gastrin inhibitor, Aphton)<br>Efaproxiral (oxygenator, Allos Therapeutics)<br>PI-88 (heparanase inhibitor, Progen)<br>Tesmilifen (histamine antagonist, YM BioSciences)<br>Histamine (histamine H2 receptor agonist, Maxim)<br>Tiazofurin (IMPDH inhibitor, Ribapharm)<br>Cilengitide (integrin antagonist, Merck KGaA) | BCX-1777 (PNP inhibitor, BioCryst)<br>Ranpirnase (ribonuclease stimulant, Alfacell)<br>Galarubicin (RNA synthesis inhibitor, Dong-A)<br>Tirapazamine (reducing agent, SRI International)<br>N-Acetylcysteine (reducing agent, Zambon)<br>R-Flurbiprofen (NF-kappaB inhibitor, Encore)<br>3CPA (NF-kappaB inhibitor, Active Biotech)<br>Seocalcitol (vitamin D receptor agonist, Leo)<br>131-I-TM-601 (DNA antagonist, TransMolecular)<br>Eflornithin (ODC inhibitor, ILEX Oncology)<br>Minodronic acid (osteoclast inhibitor, Yamanouchi)<br>Indisulam (p53 stimulant, Eisai)<br>Aplidin (PPT inhibitor, PharmaMar) |

TABLE 1-continued

| | |
|---|---|
| SR-31747 (IL-1 antagonist, Sanofi-Synthelabo) | Rituximab (CD20 antibody, Genentech) |
| CCI-779 (mTOR kinase inhibitor, Wyeth) | Gemtuzumab (CD33 antibody, Wyeth Ayerst) |
| Exisulind (PDE-V inhibitor, Cell Pathways) | PG2 (haematopoiesis promoter, Pharmagenesis) |
| CP-461 (PDE-V inhibitor, Cell Pathways) | Immunol ™ (triclosan mouthwash, Endo) |
| AG-2037 (GART inhibitor, Pfizer) | Triacetyluridine (uridine prodrug, Wellstat) |
| WX-UK1 (plasminogen activator inhibitor, Wilex) | SN-4071 (sarcoma agent, Signature BioScience) |
| PBI-1402 (PMN stimulant, ProMetic LifeSciences) | TransMID-107 ™ (immunotoxin, KS Biomedix) |
| Bortezomib (proteasome inhibitor, Millennium) | PCK-3145 (apoptosis promoter, Procyon) |
| SRL-172 (T-cell stimulant, SR Pharma) | Doranidazole (apoptosis promoter, Pola) |
| TLK-286 (glutathione-S transferase inhibitor, Telik) | CHS-828 (cytotoxic agent, Leo) |
| PT-100 (growth factor agonist, Point Therapeutics) | Trans-retinic acid (differentiator, NIH) |
| Midostaurin (PKC inhibitor, Novartis) | MX6 (apoptosis promoter, MAXIA) |
| Bryostatin-1 (PKC stimulant, GPC Biotech) | Apomine (apoptosis promoter, ILEX Oncology) |
| CDA-II (apoptosis promoter, Everlife) | Urocidin (apoptosis promoter, Bioniche) |
| SDX-101 (apoptosis promoter, Salmedix) | Ro-31-7453 (apoptosis promoter, La Roche) |
| Ceflatonin (apoptosis promoter, ChemGenex) | Brostallicin (apoptosis promoter, Pharmacia) |

The following abbreviations refer respectively to the definitions below:
aq (aqueous), h (hour), g (gram), L (liter), mg (milligram), MHz (Megahertz), min. (minute), mm (millimeter), mmol (millimole), mM (millimolar), m.p. (melting point), eq (equivalent), mL (milliliter), L (microliter), ACN (acetonitrile), AcOH (acetic acid), $CDCl_3$ (deuterated chloroform), $CD_3OD$ (deuterated methanol), $CH_3CN$ (acetonitrile), c-hex (cyclohexane), DCC (dicyclohexyl carbodiimide), DCM (dichloromethane), DIC (diisopropyl carbodiimide), DIEA (diisopropylethyl-amine), DMF (dimethylformamide), DMSO (dimethylsulfoxide), DMSO-$d_6$ (deuterated dimethylsulfoxide), EDC (1-(3-dimethyl-amino-propyl)-3-ethylcarbodiimide), ESI (Electro-spray ionization), EtOAc (ethyl acetate), $Et_2O$ (diethyl ether), EtOH (ethanol), HATU (dimethylamino-([1,2,3]triazolo[4,5-b]pyridin-3-yloxy)-methylene]-dimethyl-ammonium hexafluorophosphate), HPLC (High Performance Liquid Chromatography), i-PrOH (2-propanol), $K_2CO_3$ (potassium carbonate), LC (Liquid Chromatography), MeOH (methanol), $MgSO_4$ (magnesium sulfate), MS (mass spectrometry), MTBE (Methyl tert-butyl ether), $NaHCO_3$ (sodium bicarbonate), $NaBH_4$ (sodium borohydride), NMM (N-methyl morpholine), NMR (Nuclear Magnetic Resonance), PyBOP (benzotriazole-1-yl-oxy-trispyrrolidino-phosphonium hexafluorophosphate), RT (room temperature), Rt (retention time), SPE (solid phase extraction), TBTU (2-(1-H-benzotriazole-1-yl)-1,1,3,3-tetramethyluromium tetrafluoro borate), TEA (triethylamine), TFA (trifluoroacetic acid), THF (tetrahydrofuran), TLC (Thin Layer Chromatography), UV (Ultraviolet).

Description of the In Vitro Assays
Abbreviations:
GST=Glutathione-S-transferase
FRET=Fluorescence resonance energy transfer
HTRF®=(homogenous time resolved fluorescence)
HEPES=4-(2-hydroxyethyl)-1-piperazine ethanesulfonic acid buffer
DTT=Dithiothreitol
BSA=bovine serum albumin
CHAPS=detergent;
CHAPS=3[(3-cholamidopropyl)dimethylammonio]-1-propanesulfonate Streptavidin-XLent® is a high grade streptavidin-XL665 conjugate for which the coupling conditions have been optimized to yield a conjugate with enhanced performances for some assays, particularly those requiring high sensitivity.

Biochemical activity testing of Tankyrase 1 and 2: Autoparsylation assay

The autoparsylation assay is run in two steps: the enzymatic reaction in which GST-tagged Tankyrase-1, resp Tankyrase-2 transferred biotinylated ADP-ribose to itself from biotinylated NAD as co-substrate and the detection reaction where a time resolved FRET between cryptate labelled anti-GST bound to the GST tag of the enzyme and Xlent® labelled-streptavidin bound the biotin-parsylation residue is analysed. The autoparsylation activity was detectable directly via the increase in HTRF signal.

The autoparsylation assay is performed as 384-well HTRF® (Cisbio, Codolet, France) assay format in Greiner low volume nb 384-well microtiter plates and is used for high throughput screen. 250 nM GST-tagged Tankyrase-1 (1023-1327 aa), respectively about 250 nM GST-tagged Tankyrase-2 (873-1166 aa) and 5 µM bio-NAD (Biolog, Life science Inst., Bremen, Germany) as co-substrate are incubated in a total volume of 5 µl (50 mM HEPES, 4 mM Mg-chloride, 0.05% Pluronic F-68, 1.4 mM DTT, 0.5% DMSO, pH 7.7) in the absence or presence of the test compound (10 dilution concentrations) for 90 min at 30° C. The reaction is stopped by the addition of 1 µl 50 mM EDTA solution. 2 µl of the detection solution (1.6 µM SA-Xlent® (Cisbio, Codolet, France), 7.4 nM Anti-GST-K® (Eu-labelled anti-GST, Cisbio, Codolet, France) in 50 mM HEPES, 800 mM KF, 0.1% BSA, 20 mM EDTA, 0.1% CHAPS, pH 7.0) are added. After 1 h incubation at room temperature the HTRF is measured with an Envision multimode reader (Perkin Elmer LAS Germany GmbH) at excitation wavelength 340 nm (laser mode) and emission wavelengths 615 nm and 665 nm. The ratio of the emission signals is determined. The full value used is the inhibitor-free reaction. The pharmacological zero value used is XAV-939 (Tocris) in a final concentration of 5 µM. The inhibitory values (IC50) are determined using either the program Symyx Assay Explorer® or Condosseo® from GeneData.

Measurement of Cellular Inhibition of Tankyrase

Since Tankyrases have been described to modulate cellular level of Axin2 (Huang et al., 2009; Nature) the increase of Axin2 level is used as read-out for determination of cellular inhibition of Tankyrases in a Luminex based assay.

Cells of the colon carcinoma cell line DLD1 are plated in 96 well plates with $1.5 \times 10^4$ cells per well. Next day, cells are treated with a serial dilution of test compound in seven steps as triplicates with a final DMSO concentration of 0.3%. After 24 hours, cells are lysed in lysis buffer (20 mM Tris/HCl pH 8.0, 150 mM NaCl, 1% NP40, 10% Glycerol) and lysates are cleared by centrifugation through a 96 well filter plate (0.65 µm). Axin2 protein is isolated from cell lysates by incubation with a monoclonal anti-Axin2 antibody (R&D Systems #MAB6078) that is bound to fluorescent carboxybeads. Then, bound Axin2 is specifically detected with a polyclonal anti-Axin2 antibody (Cell Signaling #2151) and an appropriate PE-fluorescent secondary antibody. The amount of isolated Axin2 protein is determined in a Luminex$^{200}$ machine (Luminex Corporation) according to the manufacturer's instruction by counting 100 events per well. Inhibition of Tankyrase by test compounds results in higher levels of Axin2 which directly correlates with an increase of detectable fluorescence. As controls cells are treated with solvent alone (neutral control) and with a Tankyrase reference inhibitor IWR-2 (3E-06 M) which refers as control for maximum increase of Axin2. For analysis, the obtained data are normalized against the untreated solvent control and fitted for determination of the $EC_{50}$ values using the Assay Explorer software (Accelrys).

Description of the PARP1 Assay

Biochemical Activity Testing of PARP-1: Autoparsylation Assay

The autoparsylation assay is run in two steps: the enzymatic reaction in which His-tagged Parp-1 transfers biotinylated ADP-ribose/ADP-ribose to itself from biotinylated NAD/NAD as co-substrate and the detection reaction where a time resolved FRET between cryptate labelled anti-His antibody bound to the His tag of the enzyme and Xlent® labelled-streptavidin bound the biotin-parsylation residue is analysed. The autoparsylation activity is detectable directly via the increase in HTRF signal.

The autoparsylation assay is performed as 384-well HTRF® (Cisbio, Codolet, France) assay format in Greiner low volume nb 384-well microtiter plates. 35 nM His-tagged Parp-1 (human, recombinant, Enzo Life Sciences GmbH, Lorrach, Germany) and a mixture of 125 nM bio-NAD (Biolog, Life science Inst., Bremen, Germany) and 800 nM NAD as co-substrate are incubated in a total volume of 6 µl (100 mM Tris/HCl, 4 mM Mg-chloride, 0.01% IGEPAL® CA630, 1 mM DTT , 0.5% DMSO, pH 8, 13 ng/µl activated DNA (BPS Bioscience, San Diego, US)) in the absence or presence of the test compound (10 dilution concentrations) for 150 min at 23° C. The reaction is stopped by the addition of 4 µl of the Stop/detection solution (70 nM SA-Xlent® (Cisbio, Codolet, France), 2.5 nM Anti-His-K® (Eu-labelled anti-His, Cisbio, Codolet, France) in 50 mM HEPES, 400 mM KF, 0.1% BSA, 20 mM EDTA, pH 7.0). After 1 h incubation at room temperature the HTRF iss measured with an Envision multimode reader (Perkin Elmer LAS Germany GmbH) at excitation wavelength 340 nm (laser mode) and emission wavelengths 615 nm and 665 nm. The ratio of the emission signals is determined. The full value used is the inhibitor-free reaction. The pharmacological zero value used is Olaparib (LClabs, Woburn, US) in a final concentration of 1 µM. The inhibitory values (IC50) are determined using either the program Symyx Assay Explorer® or Condosseo® from GeneData.

Description of the TNKS1 and TNKS2 ELISA Assay

Biochemical activity testing of TNKS 1 and 2: activity ELISA (Autoparsylation assay)

For analysis of autoparsylation activity of TNKS 1 and 2 an activity ELISA iss performed: In the first step GST tagged TNKS is captured on a Glutathione coated plate. Then the activity assay with biotinylated NAD is performed in the absence/presence of the compounds. During the enzymatic reaction GST tagged TNKS transfers biotinylated ADP-ribose to itself from biotinylated NAD as co-substrate. For the detection streptavidin-HRP conjugate is added that binds to the biotinylated TNKS and is thereby captured to the plates. The amount of biotinylated resp. autoparsylated TNKS is detected with a luminescence substrate for HRP. The level of the luminescence signal correlats directly with the amount of autoparsylated TNKS and therefore with activity of TNKS.

The acitivity ELISA is performed in 384 well Glutathione coated microtiter plates (Express capture Glutathione coated plate, Biocat, Heidelberg, Germany). The plates are pre-equilibrated with PBS. Then the plates are incubated with 50 µl 20 ng/well GST-tagged Tnks-1 (1023-1327 aa, prepared in-house), respectively GST-tagged Tnks-2 (873-1166 aa, prepared in-house) in assay buffer (50 mM HEPES, 4 mM Mg-chloride, 0.05% Pluronic F-68, 2 mM DTT, pH 7.7) overnight at 4° C. The plates are washed 3 times with PBS-Tween-20. The wells are blocked by incubation at room temperature for 20 minutes with 50 µl blocking buffer (PBS, 0.05% Tween-20, 0.5% BSA). Afterwards the plates are washed 3 times with PBS-Tween-20. The enzymatic reaction is performed in 50 µl reaction solution (50 mM HEPES, 4 mM Mg-chloride, 0.05% Pluronic F-68, 1.4 mM DTT, 0.5% DMSO, pH 7.7) with10 µM bio-NAD (Biolog, Life science Inst., Bremen, Germany) as co-substrate in the absence or presence of the test compound (10 dilution concentrations) for 1 hour at 30° C. The reaction is stopped by 3 times washing with PBS-Tween-20. For the detection 50 µl of 20 ng/µl Streptavidin, HRP conjugate (MoBiTec, Göttingen, Germany) in PBS/0.05% Tween-20/0.01% BSA are added and the plates are incubated for 30 minutes at room temperature. After three times washing with PBS-Tween-20 50 µl of SuperSignal ELISA Femto Maximum sensitivity substrate solution (ThermoFisherScientific (Pierce), Bonn, Germany) are added. Following a 1 minute incubation at room temperature luminescence signals are measured with an Envision multimode reader (Perkin Elmer LAS Germany GmbH) at 700 nm. The full value used is the inhibitor-free reaction. The pharmacological zero value used is XAV-939 (Tocris) in a final concentration of 5 µM. The inhibitory values (IC50) are determined using either the program Symyx Assay Explorer® or Condosseo® from GeneData.

Above and below, all temperatures are indicated in ° C. In the following examples, "conventional work-up" means: water is added if necessary, the pH is adjusted, if necessary, to values between 2 and 10, depending on the constitution of the end product, the mixture is extracted with ethyl acetate or dichloromethane, the phases are separated, the organic phase is dried over sodium sulfate and evaporated, and the residue is purified by chromatography on silica gel and/or by crystallisation. Rf values on silica gel; eluent: ethyl acetate/methanol 9:1.

HPLC/MS conditions A
column: Chromolith PerformanceROD RP-18e, 100×3 mm$^2$
gradient: A:B =99:1 to 0:100 in 1.8 min
flow rate: 2.0 ml/min
eluent A: water+0.05% formic acid
eluent B: acetonitrile+0.04% formic acid
wavelength: 220 nm
mass spectroscopy: positive mode HPLC/MS conditions B
column: Chromolith PerformanceROD RP-18e, 100×3 mm$^2$
gradient: A:B=99:1 to 0:100 in 3.5 min
flow rate: 2.0 ml/min
eluent A: water+0.05% formic acid
Eluent B: acetonitrile+0.04% formic acid
wavelength: 220 nm
mass spectroscopy: positive mode $^1$H NMR was recorded on Bruker DPX-300, DRX-400 or AVII-400 spectrometer, using residual signal of deuterated solvent as internal reference. Chemical shifts (δ) are reported in ppm relative to the residual solvent signal (δ=2.49 ppm for $^1$H NMR in DMSO-d$_6$). $^1$H NMR data are reported as follows: chemical shift (multiplicity, coupling constants, and number of hydrogens). Multiplicity is abbreviated as follows: s (singlet), d (doublet), t (triplet), q (quartet), m (multiplet), br (broad).

The microwave chemistry is performed on a single mode microwave reactor Emrys™ Optimiser from Personal Chemistry.

EXAMPLE 1

Synthesis of 3-(4-tert-butyl-phenyl)-2H-[2,6]naphthyridin-1-one ("A1")

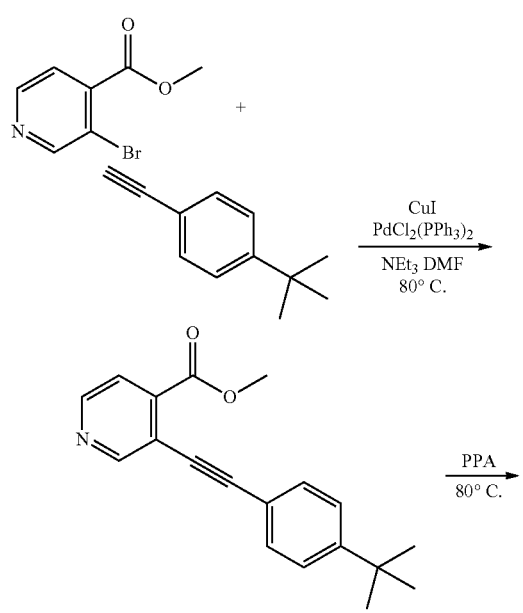

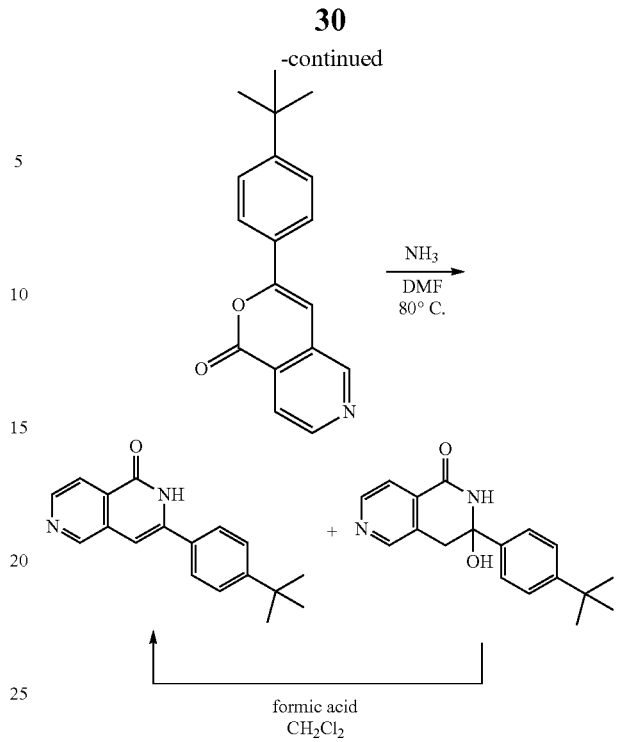

To a solution of 3-bromo-isonicotinic acid methyl ester (648 mg, 3.00 mmol) in DMF (6 ml) are added bis(triphenylphosphine)-palladium(II)-chloride (210 mg, 0.30 mmol), copper(I) iodide (17.1 mg, 0.090 mmol), triethylamine (1.25 ml, 9.00 mmol) and 1-tert-butyl-4-ethynyl-benzene (570 mg, 3.60 mmol). The resulting dark brown solution is flushed with nitrogen, heated to 80° C. and stirred in a closed reaction vial at this temperature for 3 hours. The reaction mixture is allowed to cool to room temperature and reduced in volume under vacuum. The residue is chromatographed on a silica gel column with cyclohexane/ethyl acetate as eluent to give 3-(4-tert-butyl-phenylethynyl)-isonicotinic acid methyl ester as brown oil; HPLC/MS 2.28 min (A), [M+H] 294.

A mixture of 3-(4-tert-butyl-phenylethynyl)-isonicotinic acid methyl ester (786 mg, 2.68 mmol) and polyphosphoric acid (10 g) is heated to 80° C. and stirred at this temperature for three days. The reaction mixture is allowed to cool to room temperature and water is added. The resulting precipitate is filtered off, washed with water and dried under vacuum to afford 3-(4-tert-butyl-phenyl)-pyrano[4,3-c]pyridin-1-one as olive green powder; HPLC/MS 2.16 min (A), [M+H] 280;

$^1$H NMR (400 MHz, DMSO) δ=9.08 (s, 1H), 8.76 (d, J=5.2, 1H), 8.00 (d, J=5.1, 1H), 7.86 (d, J=8.6, 2H), 7.58 (d, J=8.6, 2H), 7.55 (s, 1H), 1.33 (s, 9H).

To a suspension of 3-(4-tert-butyl-phenyl)-pyrano[4,3-c] pyridin-1-one (556 mg, 1.99 mmol) in DMF (2 ml) is added aqueous ammonia (25% by weight, 2 ml) and the mixture is stirred at 80° C. for 44 hours. The reaction mixture is diluted with water. The resulting precipitate is filtered off, washed with water and dried under vacuum to afford a mixture of 3-(4-tert-butyl-phenyl)-2H-[2,6]naphthyridin-1-one and 3-(4-tert-butyl-phenyl)-3-hydroxy-3,4-dihydro-2H-[2,6] naphthyridin-1-one. To a suspension of this material in dichloromethane (4 ml) is added formic acid (0.5 ml) and the resulting solution is stirred for 2 hours at room temperature. Then saturated sodium hydrogen carbonate solution is added. The resulting precipitate is filtered off, washed with water and dried under vacuum to afford 3-(4-tert-butyl-phenyl)-2H-[2,6]naphthyridin-1-one as off-white powder; HPLC/MS 1.88 min (A), [M+H] 279.

¹H NMR (400 MHz, DMSO) δ=11.83 (s, 1H), 9.09 (s, 1H), 8.59 (d, J=5.3, 1H), 7.98 (d, J=5.3, 1H), 7.76 (d, J=8.5, 2H), 7.53 (d, J=8.5, 2H), 7.00 (s, 1H), 1.33 (s, 9H).

EXAMPLE 2

Synthesis of 4-(1-oxo-1,2-dihydro-isoquinolin-3-yl)-benzoic acid methyl ester ("A2") and 3-[4-(1-hydroxy-1-methyl-ethyl)-phenyl]-2H-isoquinolin-1-one ("A3")

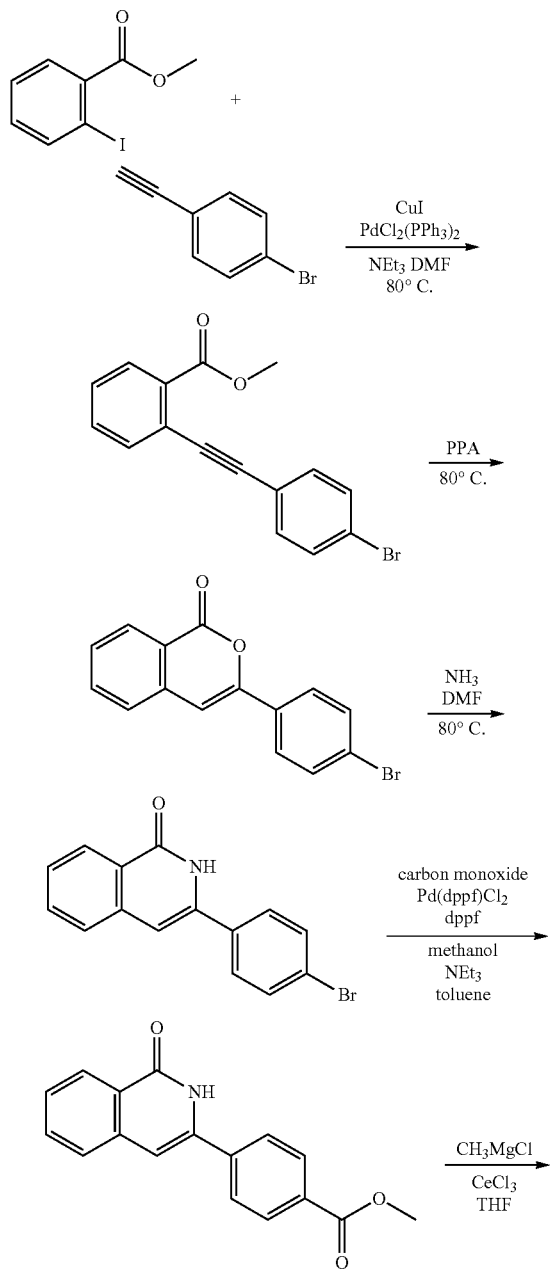

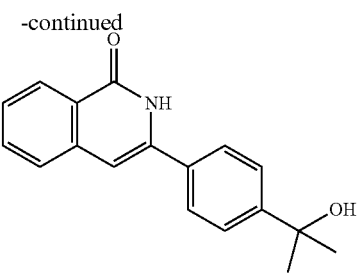

To a solution of 2-iodo-benzoic acid methyl ester (1.31 g, 5.00 mmol) in DMF (10 ml) are added bis(triphenylphosphine)-palladium(II)-chloride (351 mg, 0.50 mmol), copper (I) iodide (28.5 mg, 0.15 mmol), triethylamine (2.08 ml, 15.0 mmol) and 1-bromo-4-ethynyl-benzene (905 mg, 5.00 mmol). The resulting dark brown solution is flushed with nitrogen, heated to 80° C. and stirred in a closed reaction vial at this temperature for 16 hours. The reaction mixture is allowed to cool to room temperature and partitioned between water and dichloromethane. The organic phase is washed with 1 N HCl, dried over sodium sulfate and evaporated under vacuum. The residue is chromatographed on a silica gel column with cyclohexane/ethyl acetate as eluent to give 2-(4-bromo-phenylethynyl)-benzoic acid methyl ester as brown oil; HPLC/MS 3.46 min (B), [M+H] 315/317.

A mixture of 2-(4-bromo-phenylethynyl)-benzoic acid methyl ester (1.24 g, 3.95 mmol) and polyphosphoric acid (16 g) is heated to 80° C. and stirred at this temperature for 20 hours. The reaction mixture is allowed to cool to room temperature and water is added. The resulting precipitate is filtered off, washed with water and dried under vacuum to afford 3-(4-bromo-phenyl)-isochromen-1-one as brown powder; HPLC/MS 2.18 min (A), [M+H] 301/303.

To a suspension of 3-(4-bromo-phenyl)-isochromen-1-one (1.05 g, 3.50 mmol) in DMF (7 ml) is added aqueous ammonia (25% by weight, 7 ml) and the mixture is stirred at 80° C. for 3 days. The reaction mixture is diluted with water. The resulting precipitate is filtered off, washed with water and dried under vacuum to afford 3-(4-bromo-phenyl)-2H-isoquinolin-1-one as brown powder; HPLC/MS 1.96 min (A), [M+H] 300/302;

¹H NMR (400 MHz, DMSO) δ=11.53 (s, 1H), 8.21 (d, J=7.7, 1H), 7.72 (m, 6H), 7.50 (ddd, J=8.2, 5.4, 2.9, 1H), 6.95 (s, 1H).

In an autoclave, a solution of 3-(4-bromo-phenyl)-2H-isoquinolin-1-one (942 mg, 3.14 mmol) and triethylamine (0.70 ml, 5.04 mmol) in methanol (10 ml) and toluene (10 ml) is flushed with nitrogen. (1,1'-bis(diphenylphosphino)-ferrocene)dichloropalladium(II) (77 mg, 0.09 mmol) and 1,1-bis-(diphenyl-phosphino)-ferrocene (70 mg, 0.13 mmol) are added. Then the autoclave is filled with carbon monoxide and heated to 100° C. The autoclave is kept at this temperature for 16 hours with a carbon monoxide pressure of 2-3 bar. The autoclave is brought to atmospheric pressure and the reaction mixture is allowed to cool to room temperature. A precipitate forms, which is filtered off, washed with methanol and dried under vacuum to afford 4-(1-oxo-1,2-dihydro-isoquinolin-3-yl)-benzoic acid methyl ester as off-white needles; HPLC/MS 2.47 min (B), [M+H] 280;

1H NMR (400 MHz, DMSO) δ=11.61 (s, 1H), 8.22 (d, J=7.9, 1H), 8.05 (d, J=8.4, 2H), 7.95 m, 2H), 7.75 (d, J=3.8, 2H), 7.53 (m, 1H), 7.06 (s, 1H), 3.89 (s, 3H).

4-(7-Fluoro-1-oxo-1,2-dihydro-isoquinolin-3-yl)-benzoic acid methyl ester ("A4") is prepared analogously HPLC/MS 1.84 min (A), [M+H] 298;
$^1$H NMR (400 MHz, DMSO) δ=11.75 (s, 1H), 8.05 (d, J=8.6, 2H), 7.94 (d, J=8.6, 2H), 7.86 (m, 2H), 7.65 (td, J=8.7, 2.8, 1H), 7.10 (s, 1H), 3.89 (s, 3H).

To a suspension of 4-(1-oxo-1,2-dihydro-isoquinolin-3-yl)-benzoic acid methyl ester (494 mg, 1.77 mmol) in THF (7 ml) is added cerium(III) chloride (481 mg, 1.95 mmol). The mixture is stirred at room temperature for 1 hour. Then methylmagnesium chloride (20% solution in THF, 2.70 ml, 7.44 mmol) is added and the reaction mixture is stirred at room temperature for another hour. Carefully, water is added to the reaction mixture. The mixture is filtered through a pad of celite and partitioned between water and dichloromethane. The organic phase is dried over sodium sulfate and evaporated. The residue is triturated with tert-butylmethylether to afford 3-[4-(1-hydroxy-1-methyl-ethyl)-phenyl]-2H-isoquinolin-1-one as light yellow powder; HPLC/MS 1.66 min (A), [M+H] 280;
$^1$H NMR (400 MHz, DMSO) δ=11.46 (s, 1H), 8.20 (dd, J=7.8, 0.6, 1H), 7.72 (m, 4H), 7.58 (d, J=8.6, 2H), 7.48 (ddd, J=8.2, 5.2, 3.1, 1H), 6.90 (s, 1H), 5.11 (s, 1H), 1.46 (s, 6H).

The following compounds are prepared analogously:

6-fluoro-3-[4-(1-hydroxy-1-methyl-ethyl)-phenyl]-2H-isoquinolin-1-one ("A5")

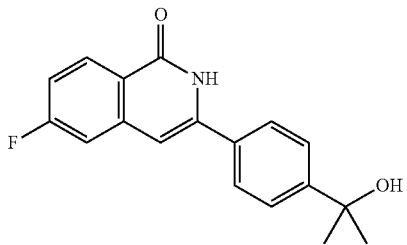 [SMILES: CC(C)(O)c1ccc(-c2cc3cc(F)ccc3c(=O)[nH]2)cc1]

HPLC/MS 1.72 min (A), [M+H] 298;
$^1$H NMR (400 MHz, DMSO) δ=11.51 (s, 1H), 8.25 (dd, J=8.9, 6.0, 1H), 7.72 (d, J=8.5, 2H), 7.58 (d, J=8.5, 2H), 7.50 (dd, J=10.0, 2.5, 1H), 7.30 (td, J=8.8, 2.6, 1H), 6.88 (s, 1H), 5.10 (s, 1H), 1.46 (s, 6H);

7-fluoro-3-[4-(1-hydroxy-1-methyl-ethyl)-phenyl]-2H-isoquinolin-1-one ("A6")

HPLC/MS 1.71 min (A), [M+H] 298;
$^1$H NMR (400 MHz, DMSO) δ=11.58 (s, 1H), 7.85 (dd, J=9.5, 2.8, 1H), 7.80 (dd, J=8.8, 5.3, 1H), 7.72 (d, J=8.5, 2H), 7.62 (m, 1H), 7.57 (d, J=8.5, 2H), 6.95 (s, 1H), 5.08 (s, 1H), 1.46 (s, 6H);

3-[4-(1-hydroxy-1-methyl-ethyl)-phenyl]-7-methyl-2H-isoquinolin-1-one ("A7")

HPLC/MS 1.76 min (A), [M+H] 294;
$^1$H NMR (300 MHz, DMSO) δ=11.35 (s, 1H), 8.01 (s, 1H), 7.72 (d, J=8.5, 2H), 7.56 (m, 4H), 6.86 (s, 1H), 5.08 (s, 1H), 2.45 (s, 3H), 1.46 (s, 6H);

3-[4-(1-hydroxy-1-methyl-ethyl)phenyl]-2H-2,6-naphthyridin-1-one ("A23")

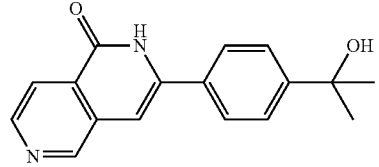 [SMILES: CC(C)(O)c1ccc(-c2cc3cnccc3c(=O)[nH]2)cc1]

HPLC/MS 1.42 min (A), [M+H] 281;
$^1$H NMR (400 MHz, DMSO) δ=11.83 (s, 1H), 9.10 (s, 1H), 8.61 (d, J=5.3, 1H), 8.00 (d, J=5.3, 1H), 7.75 (m, 2H), 7.60 (m, 2H), 7.02 (s, 1H), 5.11 (s, 1H), 1.47 (s, 6H);

3-[4-(1-hydroxy-1-methyl-ethyl)phenyl]-2H-2,7-naphthyridin-1-one ("A24")

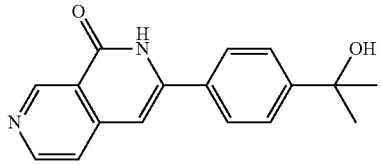 [SMILES: CC(C)(O)c1ccc(-c2cc3ccncc3c(=O)[nH]2)cc1]

HPLC/MS 1.27 min (A), [M+H] 281;
$^1$H NMR (400 MHz, DMSO) δ=11.78 (s, 1H), 9.31 (s, 1H), 8.69 (d, J=5.5, 1H), 7.75 (m, 2H), 7.60 (m, 3H), 6.89 (s, 1H), 5.12 (s, 1H), 1.46 (s, 6H);

7-chloro-3-[4-(1-hydroxy-1-methyl-ethyl)phenyl]-2H-isoquinolin-1-one ("A25")

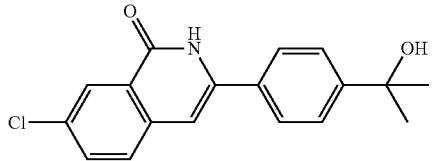 [SMILES: CC(C)(O)c1ccc(-c2cc3ccc(Cl)cc3c(=O)[nH]2)cc1]

HPLC/MS 1.83 min (A), [M+H] 314;
$^1$H NMR (400 MHz, DMSO-$d_6$) δ [ppm] 11.65 (s, 1H), 8.13 (s, 1H), 7.80-7.69 (m, 4H), 7.62-7.54 (m, 2H), 6.94 (s, 1H), 5.11 (s, 1H), 1.46 (s, 6H);

3-[4-(1-hydroxy-1-methyl-ethyl)phenyl]-5-methoxy-2H-isoquinolin-1-one ("A26")

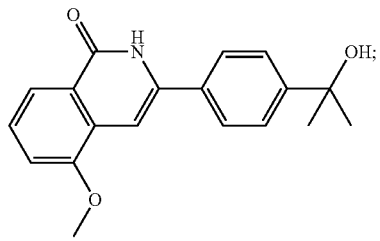 [SMILES: COc1cccc2c(=O)[nH]c(-c3ccc(C(C)(C)O)cc3)cc12]

8-fluoro-3-[4-(1-hydroxy-1-methyl-ethyl)phenyl]-2H-isoquinolin-1-one ("A27")

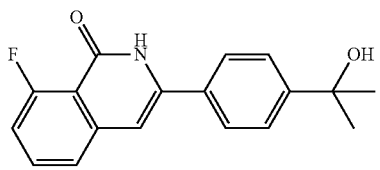 [SMILES: CC(C)(O)c1ccc(-c2cc3cccc(F)c3c(=O)[nH]2)cc1]

HPLC/MS 1.67 min (A), [M+H] 298;
<sup>1</sup>H NMR (400 MHz, DMSO-$d_6$) δ [ppm] 11.42 (s, 1H), 7.82-7.70 (m, 2H), 7.67 (td, J=8.0, 4.9 Hz, 1H), 7.62-7.53 (m, 2H), 7.50 (dd, J=8.1, 1.0 Hz, 1H), 7.16 (ddd, J=11.9, 8.0, 1.1 Hz, 1H), 6.90 (d, J=2.2 Hz, 1H), 5.10 (s, 1H), 1.46 (s, 6H);

5-fluoro-3-[4-(1-hydroxy-1-methyl-ethyl)phenyl]-2H-isoquinolin-1-one ("A28")

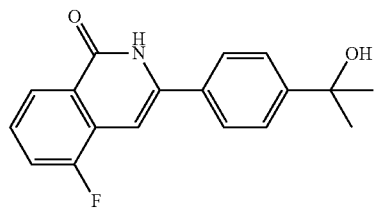 [SMILES: CC(C)(O)c1ccc(-c2cc3c(F)cccc3c(=O)[nH]2)cc1]

HPLC/MS 1.75 min (A), [M+H] 298;
<sup>1</sup>H NMR (400 MHz, DMSO-$d_6$) δ [ppm] 11.69 (s, 1H), 8.04 (d, J=8.0 Hz, 1H), 7.80-7.72 (m, 2H), 7.64-7.54 (m, 3H), 7.48 (td, J=8.0, 5.3 Hz, 1H), 6.84 (s, 1H), 5.12 (s, 1H), 1.46 (s, 6H);

5,7-difluoro-3-[4-(1-hydroxy-1-methyl-ethyl)-phenyl]-2H-isoquinolin-1-one ("A33")

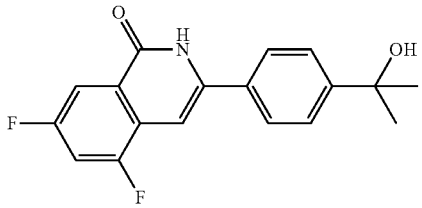 [SMILES: CC(C)(O)c1ccc(-c2cc3c(F)cc(F)cc3c(=O)[nH]2)cc1]

HPLC/MS 1.82 min (A), [M+H] 316;
<sup>1</sup>H NMR (400 MHz, DMSO-d6) δ 11.82 (s, 1H), 7.80-7.68 (m, 4H), 7.63-7.54 (m, 2H), 6.83 (s, 1H), 5.12 (s, 1H), 1.46 (s, 6H).

EXAMPLE 3

Synthesis of 3-(4-hydroxymethyl-phenyl)-2H-isoquinolin-1-one ("A8")

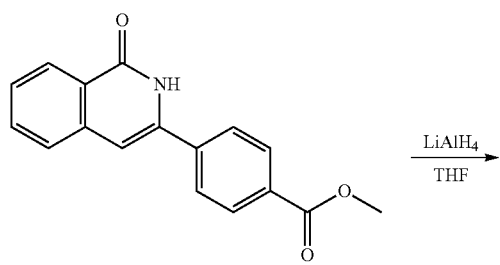

Under nitrogen, lithium aluminiumhydride (22.8 mg, 0.60 mmol) is added to a suspension of 4-(1-oxo-1,2-dihydro-isoquinolin-3-yl)-benzoic acid methyl ester (83.8 mg, 0.301 mmol) (for preparation see previous example) in THF (3 ml). The reaction mixture is stirred at ambient temperature for 16 hours. A few drops of methanol and then HCl (2 N aqueous solution, 0.5 ml) are added slowly to the reaction mixture. It is then filtered over a pad of celite. The filtrate is evaporated and the residue is triturated with tert-butyl methylether to afford 3-(4-hydroxymethyl-phenyl)-2H-isoquinolin-1-one as brown powder; HPLC/MS 1.55 min (A), [M+H] 252;

<sup>1</sup>H NMR (400 MHz, DMSO) δ=11.49 (s, 1H), 8.20 (dd, J=7.8, 0.6, 1H), 7.76 (d, J=8.3, 2H), 7.71 (m, 2H), 7.48 (ddd, J=8.2, 4.8, 3.6, 1H), 7.43 (d, J=8.4, 2H), 6.91 (s, 1H), 5.25 (s, 1H), 4.56 (s, 2H).

EXAMPLE 4

Synthesis of 7-fluoro-3-p-tolyl-2H-isoquinolin-1-one ("A9")

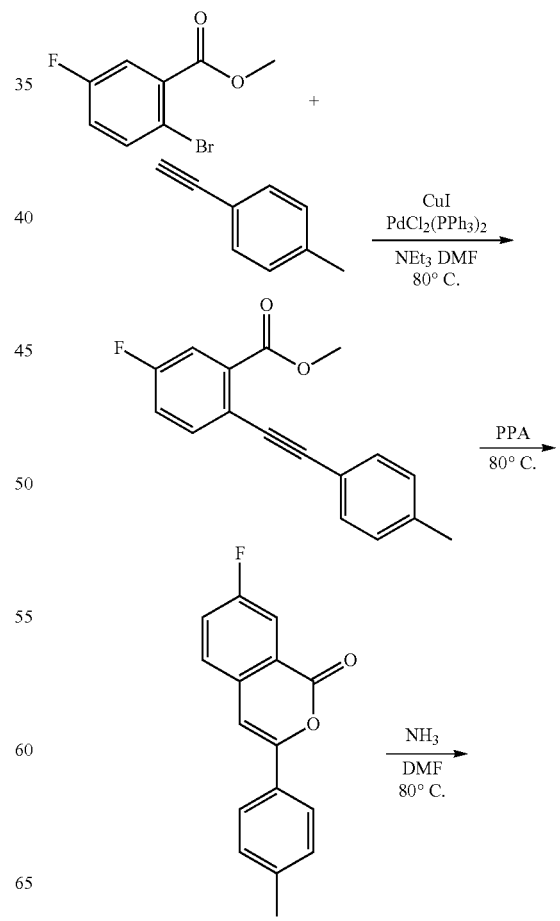

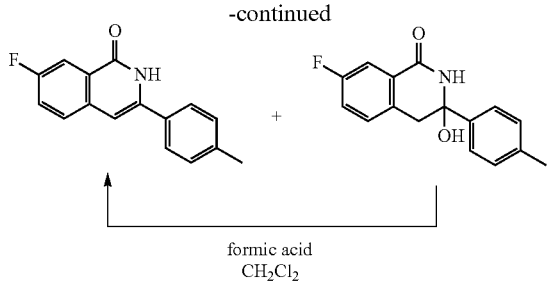

To a solution of 2-bromo-5-fluoro-benzoic acid methyl ester (466 mg, 2.00 mmol) in DMF (4 ml) are added bis(triphenylphosphine)-palladium(II)-chloride (104 mg, 0.20 mmol), copper(I) iodide (11.4 mg, 0.060 mmol), triethylamine (0.83 ml, 6.00 mmol) and 1-ethynyl-4-methyl-benzene (279 mg, 2.40 mmol).

The resulting dark brown solution is flushed with nitrogen, heated to 80° C. and stirred in a closed reaction vial at this temperature for 16 hours. The reaction mixture is allowed to cool to room temperature and partitioned between water and dichloromethane. The organic phase is washed with 1 N HCl, dried over sodium sulfate and evaporated under vacuum. The residue is chromato-graphed on a silica gel column with cyclohexane/ethyl acetate as eluent to give 5-fluoro-2-p-tolylethynyl-benzoic acid methyl ester as brown oil; HPLC/MS 2.29 min (A), [M+H] 269.

A mixture of 5-fluoro-2-p-tolylethynyl-benzoic acid methyl ester (359 mg, 1.34 mmol) and polyphosphoric acid (4 g) is heated to 80° C. and stirred at this temperature for 20 hours. The reaction mixture is allowed to cool to room temperature and water is added. The mixture is partitioned between water and dichloromethane. The organic phase is dried over sodium sulfate and evaporated. The residue is chromatographed on a silica gel column with cyclohexane/dichloromethane as eluent to afford 7-fluoro-3-p-tolyl-isochromen-1-one as off-white solid; HPLC/MS 2.16 min (A), [M+H] 255.

To a suspension of 7-fluoro-3-p-tolyl-isochromen-1-one (200 mg, 0.79 mmol) in DMF (1.5 ml) is added aqueous ammonia (25% by weight, 1.5 ml) and the mixture is stirred at 80° C. for 3 days. The reaction mixture is diluted with water. The resulting precipitate is filtered off, washed with water and dried under vacuum to afford a mixture of 7-fluoro-3-p-tolyl-2H-isoquinolin-1-one and 7-fluoro-3-hydroxy-3-p-tolyl-3,4-dihydro-2H-isoquinolin-1-one. To a suspension of this material in dichloromethane (2 ml) is added formic acid (100 μl) and the resulting solution is stirred for 8 hours at room temperature. The solution is evaporated to dryness to afford 7-fluoro-3-p-tolyl-2H-isoquinolin-1-one as white solid; HPLC/MS 1.92 min (A), [M+H] 254;

$^1$H NMR (400 MHz, DMSO) δ=11.60 (s, 1H), 7.85 (dd, J=9.5, 2.8, 1H), 7.80 (dd, J=8.8, 5.3, 1H), 7.68 (d, J=8.2, 2H), 7.62 (td, J=8.7, 2.8, 1H), 7.30 (d, J=8.0, 2H), 6.94 (s, 1H), 2.37 (s, 3H).

The following compounds are prepared analogously:

6-fluoro-3-p-tolyl-2H-isoquinolin-1-one ("A10")

HPLC/MS 1.93 min (A), [M+H] 254;

$^1$H NMR (400 MHz, DMSO) δ=11.51 (s, 1H), 8.24 (dd, J=8.9, 6.0, 1H), 7.68 (d, J=8.2, 2H), 7.49 (dd, J=10.0, 2.5, 1H), 7.30 (m, 3H), 6.87 (s, 1H), 2.37 (s, 3H);

8-fluoro-3-p-tolyl-2H-isoquinolin-1-one ("A11")

HPLC/MS 1.87 min (A), [M+H] 254;
$^1$H NMR (300 MHz, DMSO) δ=11.40 (s, 1H), 7.67 (m, 3H), 7.49 (d, J=7.3, 1H), 7.30 (d, J=8.0, 2H), 7.16 (ddd, J=12.0, 8.0, 1.0, 1H), 6.88 (d, J=2.3, 1H), 2.37 (s, 3H);

5-fluoro-3-p-tolyl-2H-isoquinolin-1-one ("A12")

HPLC/MS 1.98 min (A), [M+H] 254;
$^1$H NMR (400 MHz, DMSO) δ=11.66 (s, 1H), 8.03 (d, J=7.9, 1H), 7.72 (d, J=8.2, 2H), 7.58 (ddd, J=10.3, 8.0, 1.1, 1H), 7.47 (td, J=8.0, 5.3, 1H), 7.31 (d, J=7.9, 2H), 6.82 (s, 1H), 2.37 (s, 3H);

5-methyl-3-(p-tolyl)-2H-isoquinolin-1-one ("A29")

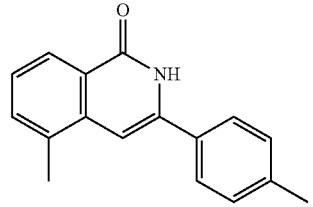 [SMILES: Cc1ccc(-c2cc3c(C)cccc3c(=O)[nH]2)cc1]

HPLC/MS 1.98 min (A), [M+H] 250;
$^1$H NMR (400 MHz, DMSO) δ=11.47 (s, 1H), 8.07 (ddt, J=8.0, 1.5, 0.7, 1H), 7.72 (m, 2H), 7.55 (ddd, J=7.2, 1.4, 0.9, 1H), 7.35 (dd, J=8.0, 7.2, 1H), 7.31 (m, 2H), 6.82 (s, 1H), 2.55 (s, 3H), 2.37 (s, 3H);

3-(p-tolyl)-5-(trifluoromethyl)-2H-isoquinolin-1-one ("A30")

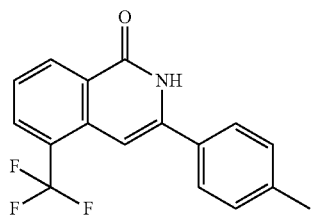 [SMILES: Cc1ccc(-c2cc3c(C(F)(F)F)cccc3c(=O)[nH]2)cc1]

HPLC/MS 2.11 min (A), [M+H] 304;
$^1$H NMR (400 MHz, DMSO) δ=11.92 (s, 1H), 8.51 (d, J=8.0, 1H), 8.13 (d, J=7.1, 1H), 7.64 (m, 3H), 7.34 (d, J=7.9, 2H), 6.72 (m, 1H), 2.38 (s, 3H).

EXAMPLE 5

Synthesis of 3-[4-(1-fluoro-1-methyl-ethyl)-phenyl]-2H-isoquinolin-1-one ("A13")

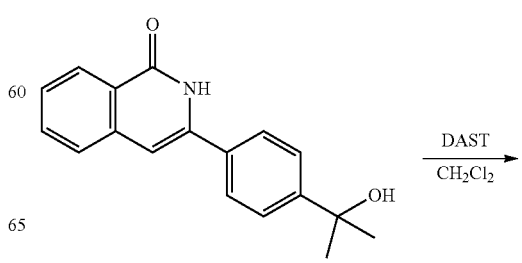

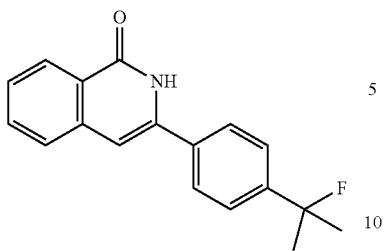

A suspension of 3-[4-(1-hydroxy-1-methyl-ethyl)-phenyl]-2H-isoquinolin-1-one (55.8 mg, 0.20 mmol) in dichloromethane (0.5 ml) is cooled to −78° C. Diethylaminosulfurtrifluoride (105 µl, 0.80 mmol) is added. The reaction mixture is allowed to reach room temperature within 30 minutes (formation of a clear solution). The reaction mixture is evaporated and the residue is treated with water and saturated sodium hydrogen carbonate solution. The solids are filtered off and chromatographed on a silica gel column with cyclohexane/ethyl acetate as eluent to afford 3-[4-(1-fluoro-1-methyl-ethyl)-phenyl]-2H-isoquinolin-1-one as fine white powder; HPLC/MS 1.94 min (A), [M+H] 282;

$^1$H NMR (400 MHz, DMSO) δ=11.49 (s, 1H), 8.22 (d, J=8.1, 1H), 7.83 (d, J=8.2, 2H), 7.73 (m 2H), 7.54 (d, J=8.4, 2H), 7.50 (ddd, J=8.2, 5.0, 3.3, 1H), 6.94 (s, 1H), 1.70 (d, J=22.2, 6H).

EXAMPLE 6

Synthesis of 3-[4-(1-Methyl-1H-pyrazol-4-yl)-phenyl]-2H-[2,7]naphthyridin-1-one ("A14")

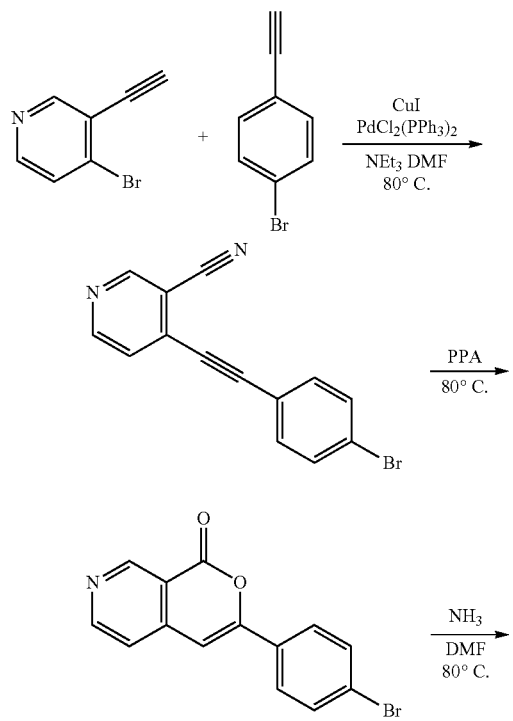

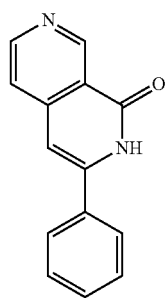

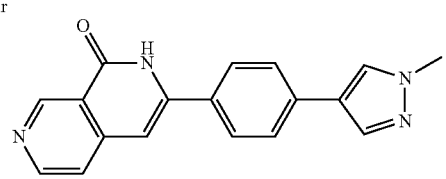

To a solution of 4-bromo-nicotinonitrile (1.10 g, 6.00 mmol) in DMF (20 ml) are added bis(triphenylphosphine)-palladium(II)-chloride (211 mg, 0.30 mmol), copper(I) iodide (34 mg, 0.18 mmol), triethylamine (1.66 ml, 12.0 mmol) and 1-bromo-4-ethynyl-benzene (1.19 g, 6.6 mmol). The mixture is flushed with nitrogen, heated to 80° C. and stirred in a closed reaction vial at this temperature for 4 hours. The reaction mixture is allowed to cool to room temperature and partitioned between water and dichloromethane. The organic phase is washed with 1 N HCl, dried over sodium sulfate and evaporated under vacuum. The residue is chromatographed on a silica gel column with cyclohexane/ethyl acetate as eluent to give 4-(4-bromo-phenylethynyl)-nicotinonitrile as light yellow powder; HPLC/MS 2.09 min (B), [M+H] 283/285.

A mixture of 4-(4-bromo-phenylethynyl)-nicotinonitrile (546 mg, 1.93 mmol) and polyphosphoric acid (8 g) is heated to 80° C. and stirred at this temperature for 20 hours. The reaction mixture is allowed to cool to room temperature and water is added. The resulting precipitate is filtered off, washed with water and triturated with saturated sodium hydrogen carbonate solution. The solids are filtered off, washed with water and dried under vacuum to afford 3-(4-bromo-phenyl)-pyrano[3,4-c]pyridin-1-one as light beige solid; HPLC/MS 1.92 min (A), [M+H] 302/304.

To a suspension of 3-(4-bromo-phenyl)-pyrano[3,4-c]pyridin-1-one (378 mg, 1.25 mmol) in DMF (3 ml) is added aqueous ammonia (25% by weight, 3 ml) and the mixture is stirred at 80° C. for 20 hours. The reaction mixture is diluted with water. The resulting precipitate is filtered off, washed with water and dried under vacuum to afford 3-(4-bromo-phenyl)-2H-[2,7]haphthyridin-1-one as yellow solid; HPLC/MS 1.48 min (A), [M+H] 301/303.

A suspension of 3-(4-bromo-phenyl)-2H-[2,7]naphthyridin-1-one (63.2 mg, 0.210 mmol), 1-methyl-4-(4,4,5,5-tetramethyl-[1,3,2]dioxaborolan-2-yl)-1H-pyrazole (65.5 mg, 0.32 mmol) and sodium hydrogen carbonate (21.2 mg, 0.25 mmol) in DMF (1 ml) and water (0.25 ml) is flushed with nitrogen and heated to 40° C. Then bis(triphenylphosphine)-palladium(II)-chloride (3.0 mg, 0.004 mmol) is added. The reaction mixture is heated to 80° C. and stirred at this temperature for 20 hours. The mixture is allowed to cool to room temperature and excess water is added. The resulting precipitate is filtered off washed with water and dried under vacuum to afford 3-[4-(1-methyl-1H-pyrazol-4-yl)-phenyl]-2H-[2,7]naphthyridin-1-one as olive green solid; HPLC/MS 1.33 min (A), [M+H] 303;

$^1$H NMR (400 MHz, DMSO) δ=11.80 (s, 1H), 9.31 (s, 1H), 8.69 (d, J=5.5, 1H), 8.26 (s, 1H), 7.98 (s, 1H), 7.82 (d, J=8.5, 2H), 7.72 (d, J=8.5, 2H), 7.59 (d, J=5.1, 1H), 6.94 (s, 1H), 3.89 (s, 3H).

EXAMPLE 7

Synthesis of 3-[4-(1-methoxy-1-methyl-ethyl)-phenyl]-2H-isoquinolin-1-one ("15")

To a suspension of 3-[4-(1-hydroxy-1-methyl-ethyl)-phenyl]-2H-isoquinolin-1-one (83.8 mg, 0.30 mmol) in methanol (1 ml) is added toluene-4-sulfonic acid monohydrate (5.2 mg, 0.030 mmol). The reaction mixture is stirred for 5 days at ambient temperature. The reaction mixture, a white suspension, is evaporated and the residue is chromatographed on a silica gel column with cyclohexane/ethyl acetate as eluent to afford 3-[4-(1-methoxy-1-methyl-ethyl)-phenyl]-2H-isoquinolin-1-one as white crystals; HPLC/MS 2.66 min (B), [M+H] 294;

$^1$H NMR (400 MHz, DMSO) δ=11.45 (s, 1H), 8.22 (dd, J=7.8, 0.7, 1H), 7.81 (d, J=8.6, 2H), 7.73 (m, 2H), 7.50 (m, 3H), 6.94 (s, 1H), 3.04 (s, 3H), 1.50 (s, 6H).

EXAMPLE 8

Synthesis of 7-fluoro-3-{4-[1-(2-hydroxy-ethoxy)-1-methyl-ethyl]-phenyl}-2H-isoquinolin-1-one ("A16") and 7-fluoro-3-(4-isopropenyl-phenyl)-2H-isoquinolin-1-one ("A17")

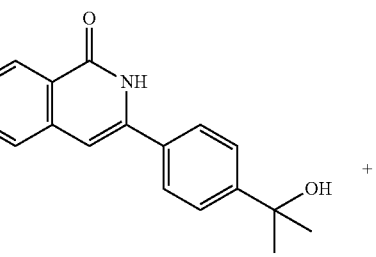
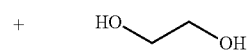
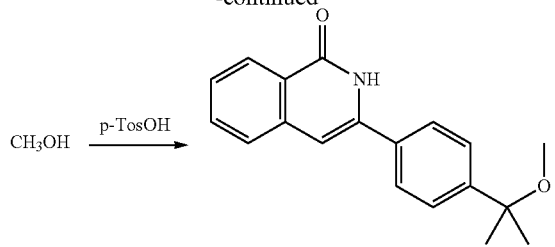
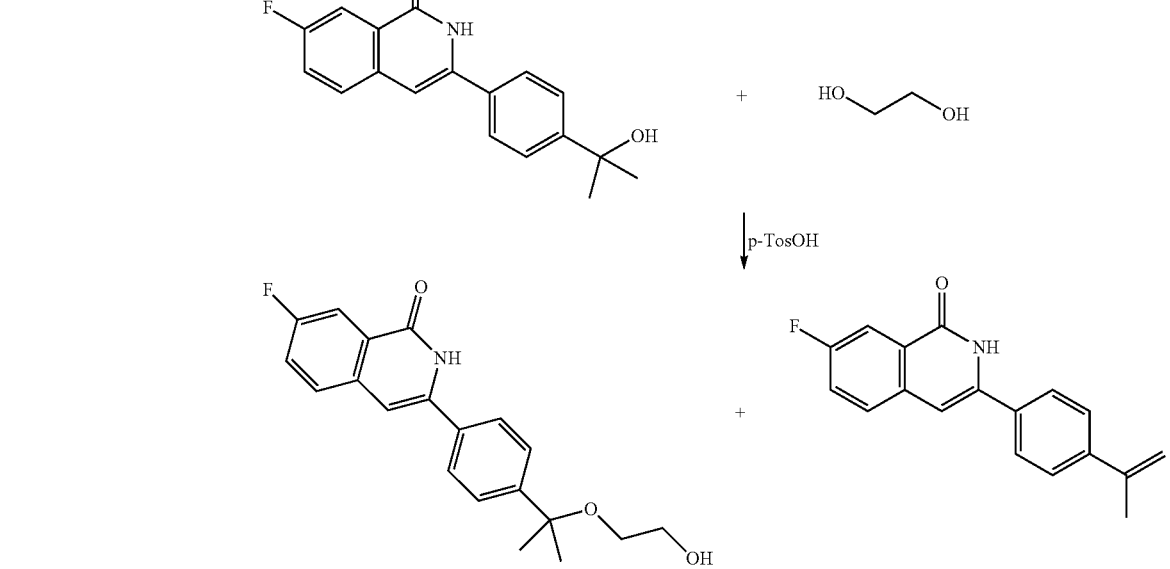
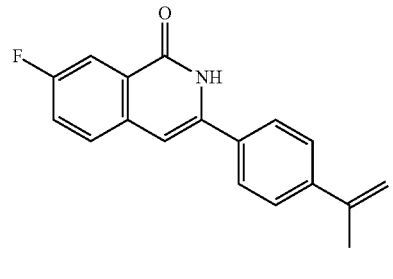

To a suspension of 7-fluoro-3-[4-(1-hydroxy-1-methyl-ethyl)-phenyl]-2H-isoquinolin-1-one (29.7 mg, 0.10 mmol) in ethane-1,2-diol (0.9 ml) is added toluene-4-sulfonic acid monohydrate (3.8 mg, 0.020 mmol). The reaction mixture is stirred for 11 days at ambient temperature. The reaction mixture is partitioned between water and dichloromethane. The organic phase is dried over sodium sulfate and evaporated. The residue is chromato-graphed on a silica gel column with cyclohexane/ethyl acetate as eluent to afford two products:

7-fluoro-3-{4-[1-(2-hydroxy-ethoxy)-1-methyl-ethyl]-phenyl}-2H-isoquinolin-1-one as white solid; HPLC/MS 1.73 min (A), [M+H] 342

$^1$H NMR (400 MHz, DMSO) δ=11.60 (s, 1H), 7.86 (dd, J=9.5, 2.8, 1H), 7.81 (dd, J=8.8, 5.4, 1H), 7.77 (d, J=8.4, 2H), 7.63 (td, J=8.7, 2.8, 1H), 7.55 (d, J=8.5, 2H), 6.98 (s, 1H), 4.56 (t, J=5.4, 1H), 3.50 (q, J=5.3, 2H), 3.19 (t, J=5.6, 2H), 1.50 (s, 6H) and 7-fluoro-3-(4-isopropenyl-phenyl)-2H-isoquinolin-1-one as white solid HPLC/MS 2.05 min (A), [M+H] 280;
$^1$H NMR (400 MHz, DMSO) δ=11.64 (s, 1H), 7.86 (dd, J=9.5, 2.8, 1H), 7.82 (dd, J=8.9, 5.4, 1H), 7.79 (d, J=8.5, 2H), 7.63 (m, 3H), 7.01 (s, 1H), 5.54 (s, 1H), 5.18 (m, 1H), 2.15 (s, 3H).

EXAMPLE 9

Synthesis of 7-fluoro-3-[4-(1-methyl-1H-pyrazol-4-yl)-phenyl]-2H-isoquinolin-1-one ("A18")

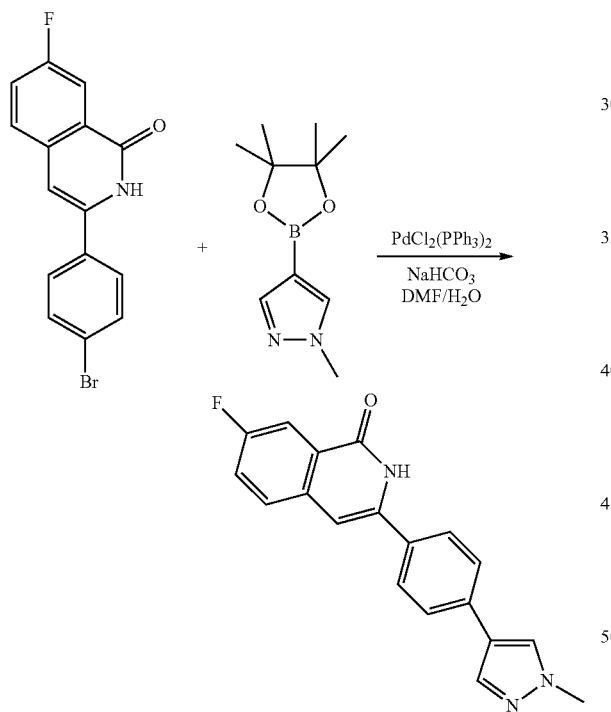

A suspension of 3-(4-bromo-phenyl)-7-fluoro-2H-isoquinolin-1-one (159 mg, 0.50 mmol), 1-methyl-4-(4,4,5,5-tetramethyl-[1,3,2]dioxaborolan-2-yl)-1H-pyrazole (114 mg, 0.55 mmol) and sodium hydrogen carbonate (50.4 mg, 0.60 mmol) in DMF (1 ml) and water (0.5 ml) is flushed with nitrogen and heated to 40° C. Then bis(triphenylphosphine)-palladium(II)-chloride (7.0 mg, 0.01 mmol) is added. The reaction mixture is heated to 80° C. and stirred at this temperature for 20 hours. The mixture is allowed to cool to room temperature and excess water is added. The resulting precipitate is filtered off and washed with water. The residue is chromatographed on a silica gel column with methanol/dichloromethane to afford 7-fluoro-3-[4-(1-methyl-1H-pyra-zol-4-yl)-phenyl]-2H-isoquinolin-1-one as ochre solid; HPLC/MS 2.43 min (B), [M+H] 320;

$^1$H NMR (500 MHz, DMSO) δ=11.60 (s, 1H), 8.24 (s, 1H), 7.96 (d, J=0.4, 1H), 7.86 (dd, J=9.4, 2.8, 1H), 7.80 (m, 3H), 7.69 (d, J=8.5, 2H), 7.62 (td, J=8.7, 2.8, 1H), 7.00 (s, 1H), 3.88 (s, 3H).

EXAMPLE 10

Synthesis of 3-[4-(1-Methyl-1H-pyrazol-4-yl)-phenyl]-2H-[2,6]naphthyridin-1-one ("A19")

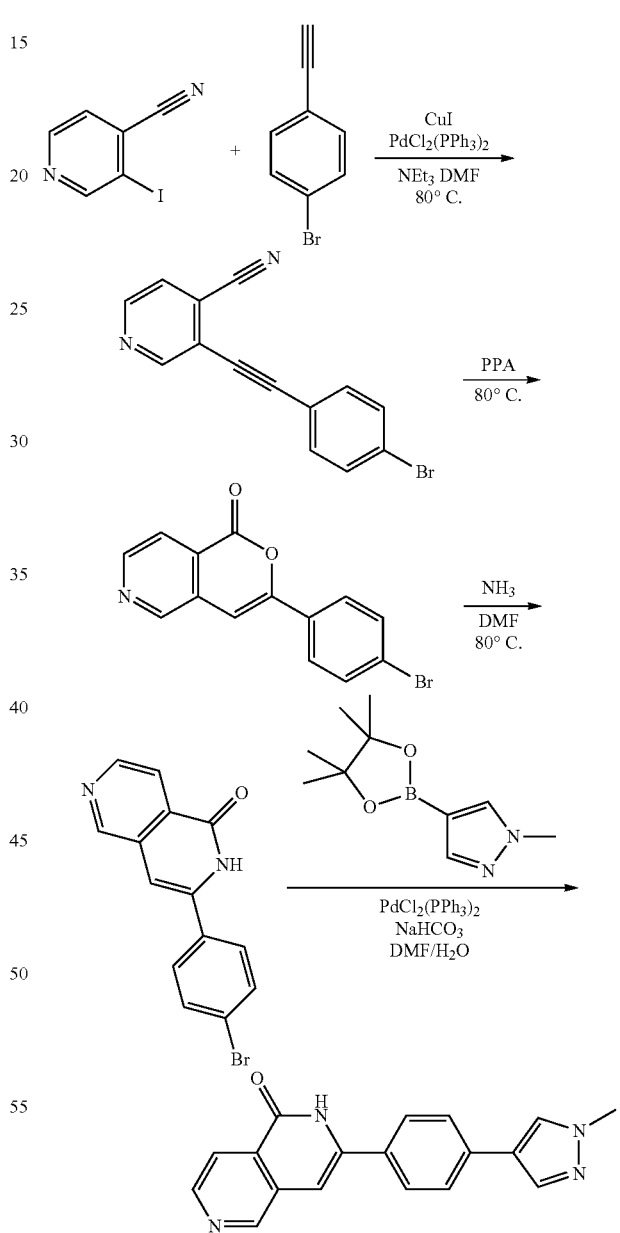

To a solution of 3-iodo-isonicotinonitrile (911 mg, 3.96 mmol) in DMF (10 ml) are added bis(triphenylphosphine)-palladium(II)-chloride (139 mg, 0.20 mmol), copper(I) iodide (22.6 mg, 0.12 mmol), triethylamine (1.10 ml, 7.9 mmol) and 1-bromo-4-ethynyl-benzene (716 mg, 3.96 mmol). The mixture is flushed with nitrogen, heated to 80° C.

and stirred in a closed reaction vial at this temperature for 18 hours. The reaction mixture is allowed to cool to room temperature and partitioned between dichloromethane and 1 N HCl. The organic phase is dried over sodium sulfate and evaporated. The residue is chromatographed on a silica gel column with cyclohexane/ethyl acetate as eluent to give 3-(4-bromo-phenylethynyl)-isonicotinonitrile as beige solid; HPLC/MS 2.13 min (A), [M+H] 283/285.

A mixture of 3-(4-bromo-phenylethynyl)-isonicotinonitrile (855 mg, 3.02 mmol) and polyphosphoric acid (8 g) is heated to 80° C. and stirred at this temperature for 4 days. The reaction mixture is allowed to cool to room temperature and water is added. The resulting precipitate is filtered off, washed with water and dried under vacuum to afford 3-(4-bromo-phenyl)-pyrano[4,3-c]pyridin-1-one as grey solid; HPLC/MS 1.98 min (A), [M+H] 302/304.

To a suspension of 3-(4-bromo-phenyl)-pyrano[4,3-c]pyridin-1-one (622 mg, 2.06 mmol) in DMF (4 ml) is added aqueous ammonia (25% by weight, 4 ml) and the mixture is stirred at 80° C. for 20 hours. The reaction mixture is diluted with water. The resulting precipitate is filtered off, washed with water, dried under vacuum and suspended in dichloromethane (4 ml). Trifluoroacetic acid (400 μl) is added and the mixture is stirred overnight at room temperature. The solid is filtered off and washed with dichloromethane. The residue is triturated with saturated aqueous sodium hydrogen carbonate solution. The solid is filtered off, washed with water and dried under vacuum to afford 3-(4-bromo-phenyl)-2H-[2,6]haphthyridin-1-one as grey solid; HPLC/MS 1.66 min (A), [M+H] 301/303.

A suspension of 3-(4-bromo-phenyl)-2H-[2,6]naphthyridin-1-one (55.0 mg, 0.18 mmol), 1-methyl-4-(4,4,5,5-tetramethyl-[1,3,2]dioxaborolan-2-yl)-1H-pyrazole (57 mg, 0.27 mmol) and sodium hydrogen carbonate (18.4 mg, 0.22 mmol) in DMF (0.5 ml) and water (0.25 ml) is flushed with nitrogen and heated to 40° C. Then bis(triphenylphosphine)-palladium(II)-chloride (2.6 mg, 0.004 mmol) is added. The reaction mixture is heated to 80° C. and stirred at this temperature for 20 hours. The mixture is allowed to cool to room temperature and excess water is added. The resulting precipitate is filtered off washed with water and 2-propanol and dried under vacuum to afford 3-[4-(1-methyl-1H-pyrazol-4-yl)-phenyl]-2H-[2,6]naphthyridin-1-one as grey solid; HPLC/MS 1.47 min (A), [M+H] 303;

$^1$H NMR (500 MHz, DMSO) δ=11.84 (s, 1H), 9.11 (s, 1H), 8.61 (d, J=5.3, 1H), 8.26 (s, 1H), 8.00 (d, J=5.3, 1H), 7.97 (d, J=0.4, 1H), 7.81 (d, J=8.5, 2H), 7.71 (d, J=8.5, 2H), 7.07 (s, 1H), 3.89 (s, 3H).

EXAMPLE 11

Synthesis of 3-[4-(1-amino-1-methyl-ethyl)phenyl]-7-fluoro-2H-isoquinolin-1-one ("A20")

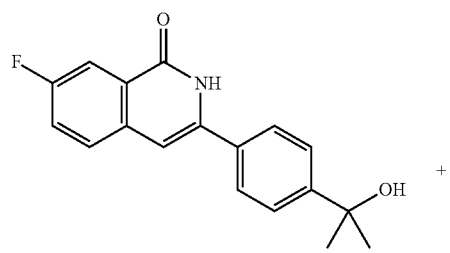

+

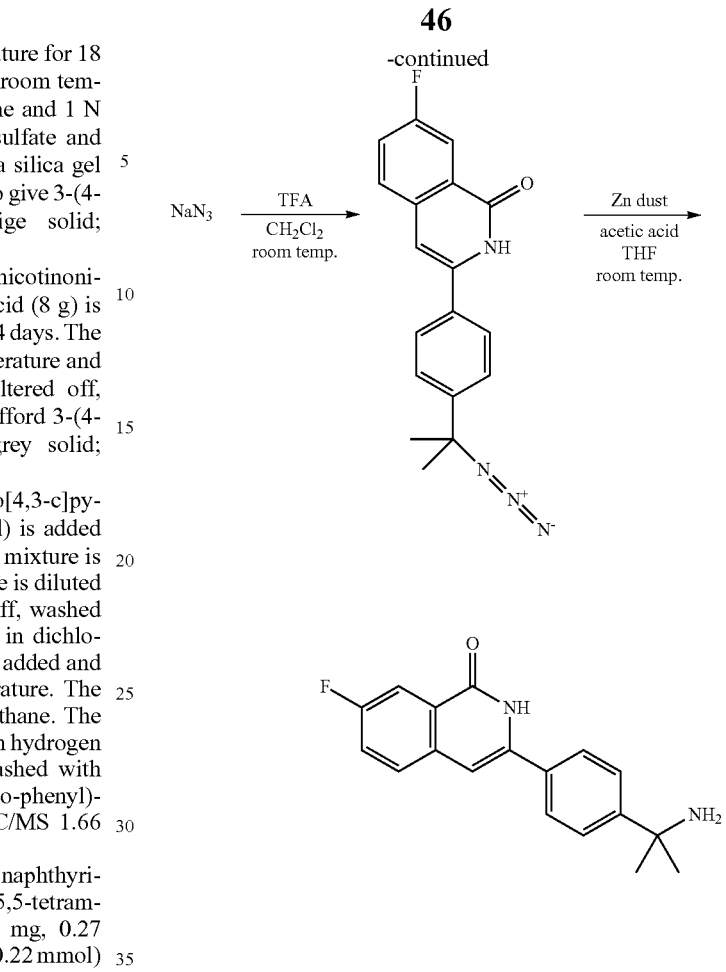

To a suspension of 7-fluoro-3-[4-(1-hydroxy-1-methyl-ethyl)-phenyl]-2H-isoquinolin-1-one (149 mg, 0.50 mmol) and sodium azide (71.5 mg, 1.10 mmol) in dichloromethane (1 ml) is added a solution of trifluoroacetic acid (316 μl, 4.1 mmol) in dichloromethane (0.5 ml) dropwise under external cooling with ice. The reaction mixture is stirred for 2 hours at room temperature. Water and 25% aqueous ammonia (0.5 ml) are added. The organic phase is separated and the aqueous phase is extracted with dichloromethane. The combined organic phases are dried over sodium sulfate and evaporated to afford 3-[4-(1-azido-1-methyl-ethyl)-phenyl]-7-fluoro-2H-isoquinolin-1-one as white powder; HPLC/MS 2.07 min (A), [M+H] 323.

To a solution of 3-[4-(1-azido-1-methyl-ethyl)-phenyl]-7-fluoro-2H-isoquinolin-1-one (141 mg, 0.44 mmol) in 4 ml THF are added zinc dust (143 mg, 2.19 mmol) and acetic acid (250 μl, 4.37 mmol) and the mixture is stirred for 18 hours at room temperature. The suspension is diluted with THF and acidified with a small amount of 25% hydrochloric acid to obtain a clear solution. More THF and methanol are added. The mixture is filtered and the filtrate is evaporated. The residue is triturated with water, the solids are filtered off, washed with water and dried under vacuum to afford 3-[4-(1-amino-1-methyl-ethyl)-phenyl]-7-fluoro-2H-isoquinolin-1-one hydrochloride as white solid;

HPLC/MS 1.35 min (A), [M+H] 297;

$^1$H NMR (400 MHz, DMSO-$d_6$) δ [ppm] 11.70 (s, 1H), 8.79 (s, 3H), 7.91-7.78 (m, 4H), 7.73-7.68 (m, 2H), 7.64 (td, J=8.7, 2.8 Hz, 1H), 7.04 (s, 1H), 1.68 (s, 6H).

EXAMPLE 12

Synthesis of 7-fluoro-3-[4-(2-methyltetrahydrofuran-2-yl)phenyl]-2H-isoquinolin-1-one ("A21")

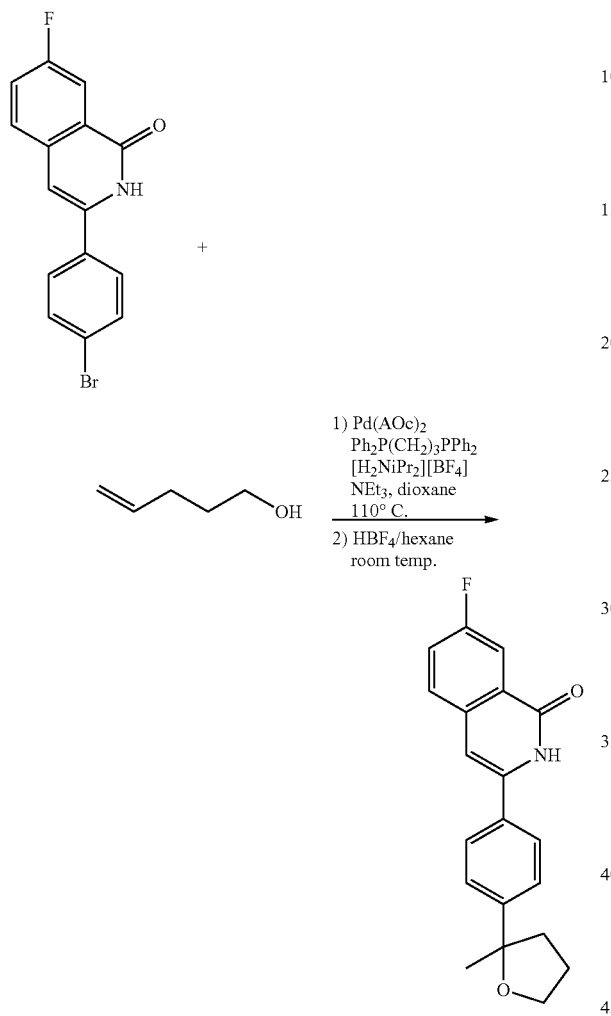

Prepared following M. McConville et al., Org. Biomol. Chem., 2010, 8, 5614-5619.

3-(4-Bromo-phenyl)-7-fluoro-2H-isoquinolin-1-one (159 mg, 0.50 mmol), palladium(II)acetate (5.6 mg, 0.03 mmol), 1,3-bis-(diphenylphosphino)-propane (21.3 mg, 0.05 mmol), 4-pentene-1-ol (51.7 mg, 0.60 mmol) and diisopropylammonium-tetrafluoroborate (142 mg, 0.75 mmol) are weighed into a reaction vial. 1,4-Dioxane (1 ml) is added and the reaction vial is flushed with nitrogen. The resulting suspension is stirred for 1 minute, triethylamine (208 µl, 1.50 mmol) is added and the reaction vial is flushed with nitrogen and closed. The reaction mixture is stirred overnight at 110° C. The reaction mixture is allowed to cool to room temperature. n-Heptane (1.5 ml) and tetrafluoroboric acid (0.21 ml, 54% solution in diethylether, 1.5 mmol) are added and the resulting biphasic mixture is stirred vigorously at room temperature for 3 hours. Triethylamine (69 µl, 0.5 mmol) is added and the reaction mixture is then partitioned between water and dichloromethane. The organic phase is dried over sodium sulfate and evaporated. The residue is chromatographed on a silica gel column with cyclohexane/ethyl acetate as eluent to afford 7-fluoro-3-[4-(2-methyl-tetrahydro-furan-2-yl)-phenyl]-2H-isoquinolin-1-one as white powder; HPLC/MS 2.78 min. (B), [M+H] 324; $^1$H NMR (500 MHz, DMSO-d$_6$) δ [ppm] 11.58 (s, 1H), 7.85 (dd, J=9.5, 2.8 Hz, 1H), 7.80 (dd, J=8.8, 5.3 Hz, 1H), 7.77-7.71 (m, 2H), 7.62 (td, J=8.7, 2.8 Hz, 1H), 7.53-7.46 (m, 2H), 6.95 (s, 1H), 3.94 (td, J=7.8, 6.4 Hz, 1H), 3.83 (td, J=8.0, 5.7 Hz, 1H), 2.11 (ddd, J=12.0, 8.0, 5.7 Hz, 1H), 2.04 (dt, J=11.9, 7.4 Hz, 1H), 1.97 (dtt, J=15.4, 7.7, 5.6 Hz, 1H), 1.74 (dqd, J=12.0, 7.6, 6.4 Hz, 1H), 1.46 (s, 3H).

EXAMPLE 13

Synthesis of 7-fluoro-3-[4-(3-hydroxyoxetan-3-yl)phenyl]-2H-isoquinolin-1-one ("A22")

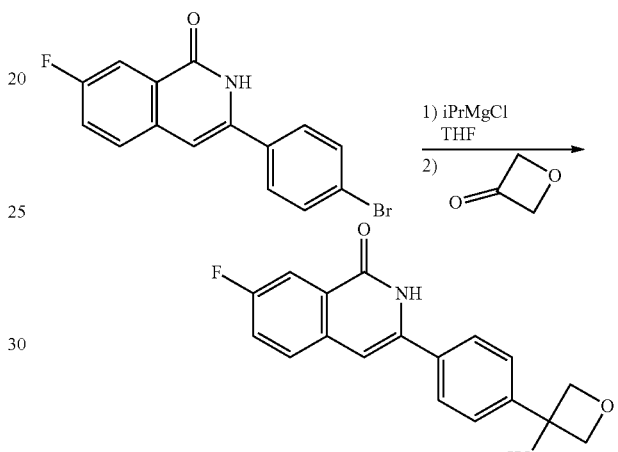

Analogously, the following compound is prepared:

7-fluoro-3-[4-(1-hydroxycyclopropyl)phenyl]-2H-isoquinolin-1-one ("A31")

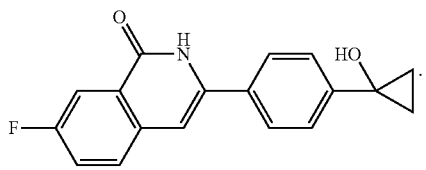 [SMILES: O=c1[nH]c(-c2ccc(C3(O)CC3)cc2)cc2ccc(F)cc12]

EXAMPLE 14

Synthesis of 7-chloro-3-[4-(1-methyl-1H-pyrazol-4-yl)-phenyl]-2H-isoquinolin-1-one ("A32")

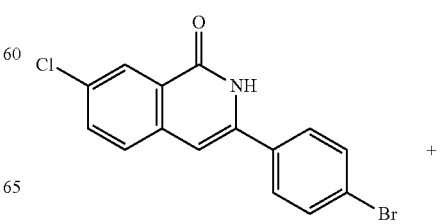

-continued

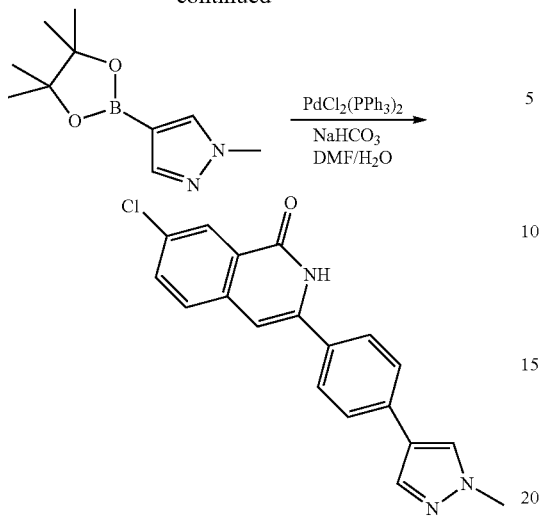

The reaction is carried out as described in example 6 (last step).

7-Chloro-3-[4-(1-methyl-1H-pyrazol-4-yl)-phenyl]-2H-isoquinolin-1-one is obtained as grey solid; HPLC/MS 1.87 min (A), [M+H] 336; $^1$H NMR (400 MHz, DMSO-$d_6$) δ [ppm] 11.66 (s, 1H), 8.25 (s, 1H), 8.13 (s, 1H), 7.97 (s, 1H), 7.84-7.77 (m, 2H), 7.75 (m, 2H), 7.69 (d, J=8.4 Hz, 2H), 6.99 (s, 1H), 3.88 (s, 3H).

Pharmacological Data

TABLE 2

Inhibition of tankyrases of some representative compounds of the formula I

| Compound No. | $IC_{50}$ tankyrase 1 (enzyme assay) | $IC_{50}$ tankyrase 2 (enzyme assay) | $EC_{50}$ tankyrase 1/2 (cell assay) |
| --- | --- | --- | --- |
| "A1" | A | B | A |
| "A2" | A | A | B |
| "A3" | A | A | A |
| "A4" | B | B | B |
| "A5" | A | B | B |
| "A6" | A | A | A |
| "A7" | B | B | B |
| "A8" | A | B | A |
| "A9" | A | A | B |
| "A10" | B | B | C |
| "A11" | A | A | B |
| "A12" | A | B | B |
| "A13" | A | B | B |
| "A14" | A | B | B |
| "A15" | A | B | A |
| "A16" | A | A | A |
| "A17" | A | B | A |
| "A18" | A | B | A |
| "A19" | B | B | |
| "A20" | A | A | B |
| "A21" | A | B | B |
| "A23" | A | A | B |
| "A24" | A | A | B |
| "A25" | A | B | B |
| "A27" | A | A | A |
| "A28" | A | A | A |
| "A29" | A | B | B |
| "A30" | B | C | |
| "A32" | A | B | B |
| "A33" | A | B | A |

$IC_{50}$: <0.3 μM = A  0.3-3 μM = B  3-50 μM = C

TABLE 3

Inhibition of tankyrases of some representative compounds of the formula I

| Compound No. | $IC_{50}$ PARP | $IC_{50}$ TNKS1 ELISA | $IC_{50}$ TNKS2 ELISA |
| --- | --- | --- | --- |
| "A1" | | A | |
| "A3" | B | A | A |
| "A9" | A | A | A |
| "A10" | C | A | A |
| "A14" | C | A | A |
| "A5" | B | A | A |
| "A15" | B | A | A |
| "A6" | B | A | A |
| "A18" | B | A | A |
| "A11" | B | A | A |
| "A12" | B | A | A |
| "A16" | B | A | A |
| "A17" | B | A | A |
| "A20" | A | A | A |
| "A27" | B | A | A |
| "A28" | B | A | A |
| "A29" | A | A | A |
| "A23" | C | A | A |
| "A24" | C | A | A |
| "A33" | A | A | A |

$IC_{50}$: <0.3 μM = A  0.3-3 μM = B  3-50 μM = C

The compounds shown in Table 3 are particularly preferred compounds according to the invention.

The compounds shown in Table 1 are particularly preferred compounds according to the invention.

The following examples relate to medicaments:

EXAMPLE A

Injection Vials

A solution of 100 g of an active ingredient of the formula I and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of an active ingredient of the formula I with 100 g of soya lecithin and 1400 g of cocoa butter is melted, poured into moulds and allowed to cool. Each suppository contains 20 mg of active ingredient.

EXAMPLE C

Solution

A solution is prepared from 1 g of an active ingredient of the formula I, 9.38 g of $NaH_2PO_4 \cdot 2 H_2O$, 28.48 g of $Na_2HPO_4 \cdot 12 H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active ingredient of the formula I are mixed with 99.5 g of Vaseline under aseptic conditions.

EXAMPLE E

Tablets

A mixture of 1 kg of active ingredient of the formula I, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

EXAMPLE F

Dragees

Tablets are pressed analogously to Example E and subsequently coated in a conventional manner with a coating of sucrose, potato starch, talc, tragacanth and dye.

EXAMPLE G

Capsules 2 kg of active ingredient of the formula I are introduced into hard gelatine capsules in a conventional manner in such a way that each capsule contains 20 mg of the active ingredient.

EXAMPLE H

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

The invention claimed is:

1. A compound which is

| No. | Name |
|---|---|
| "A3" | 3-[4-(1-hydroxy-1-methyl-ethyl)-phenyl]-2H-isoquinolin-1-one |
| "A5" | 6-fluoro-3-[4-(1-hydroxy-1-methyl-ethyl)-phenyl]-2H-isoquinolin-1-one |
| "A6" | 7-fluoro-3-[4-(1-hydroxy-1-methyl-ethyl)-phenyl]-2H-isoquinolin-1-one |
| "A7" | 3-[4-(1-hydroxy-1-methyl-ethyl)-phenyl]-7-methyl-2H-isoquinolin-1-one |
| "A8" | 3-(4-hydroxymethyl-phenyl)-2H-isoquinolin-1-one |
| "A16" | 7-fluoro-3-{4-[1-(2-hydroxy-ethoxy)-1-methyl-ethyl]-phenyl}-2H-isoquinolin-1-one |
| "A20" | 3-[4-(1-amino-1-methyl-ethyl)phenyl]-7-fluoro-2H-isoquinolin-1-one |
| "A23" | 3-[4-(1-hydroxy-1-methyl-ethyl)phenyl]-2H-2,6-naphthyridin-1-one |
| "A24" | 3-[4-(1-hydroxy-1-methyl-ethyl)phenyl]-2H-2,7-naphthyridin-1-one |
| "A25" | 7-chloro-3-[4-(1-hydroxy-1-methyl-ethyl)phenyl]-2H-isoquinolin-1-one |
| "A26" | 3-[4-(1-hydroxy-1-methyl-ethyl)phenyl]-5-methoxy-2H-isoquinolin-1-one |
| "A27" | 8-fluoro-3-[4-(1-hydroxy-1-methyl-ethyl)phenyl]-2H-isoquinolin-1-one |
| "A28" | 5-fluoro-3-[4-(1-hydroxy-1-methyl-ethyl)phenyl]-2H-isoquinolin-1-one or |
| "A33" | 5,7-difluoro-3-[4-(1-hydroxy-1-methyl-ethyl)-phenyl]-2H-isoquinolin-1-one | or a pharmaceutically acceptable solvate, salt, tautomer or stereoisomer thereof, or a mixture thereof in all ratios.

2. A medicament comprising at least one compound of claim 1 or a pharmaceutically acceptable salt, solvate, tautomer or stereoisomer thereof, or a mixture thereof in all ratios, and optionally a pharmaceutically acceptable carrier, excipient or vehicle.

3. A medicament comprising at least one compound of claim 1 or a pharmaceutically acceptable salt, solvate, tautomer or stereoisomer thereof, or a mixture thereof in all ratios, and at least one further medicament active ingredient.

4. A kit consisting of separate packs of
  (a) an effective amount of a compound of claim 1 or a pharmaceutically acceptable salt, solvate, tautomer or stereoisomer thereof, or a mixture thereof in all ratios, and
  (b) an effective amount of a further medicament active ingredient.

* * * * *